United States Patent
Corl et al.

(10) Patent No.: US 6,913,581 B2
(45) Date of Patent: Jul. 5, 2005

(54) HIGH OUTPUT THERAPEUTIC ULTRASOUND TRANSDUCER

(76) Inventors: Paul D. Corl, 3883 El Centro St., Palo Alto, CA (US) 94306; John McKenzie, 1742 Eaton Ave., San Carlos, CA (US) 94070; Joseph Karratt, 380 Vallejo Dr., #223, Millbrae, CA (US) 94070; Gary Hulme, 4365 Lonardo Ave., San Jose, CA (US) 95118-1950

( * ) Notice: Subject to any disclaimer, the term of this patent is extended or adjusted under 35 U.S.C. 154(b) by 104 days.

(21) Appl. No.: 10/281,397

(22) Filed: Oct. 24, 2002

(65) Prior Publication Data

US 2003/0109812 A1 Jun. 12, 2003

Related U.S. Application Data

(63) Continuation-in-part of application No. 09/813,277, filed on Mar. 20, 2001, now Pat. No. 6,508,775, which is a continuation-in-part of application No. 09/531,027, filed on Mar. 20, 2000, now Pat. No. 6,432,068.

(51) Int. Cl.[7] .................................................. A61H 1/00
(52) U.S. Cl. ....................... 601/2; 601/1; 601/3; 601/4; 600/437; 600/439
(58) Field of Search .......................... 601/1–5; 600/439, 600/437; 606/2–5, 27; 602/2

(56) References Cited

U.S. PATENT DOCUMENTS

| | | |
|---|---|---|
| 5,069,664 A | 12/1991 | Guess et al. |
| 5,334,183 A | 8/1994 | Wuchinich |
| 5,725,494 A | 3/1998 | Brisken |
| 5,735,811 A | 4/1998 | Brisken |
| 6,016,023 A | 1/2000 | Nilsson et al. |
| 6,024,718 A | 2/2000 | Chen et al. |
| 6,432,068 B1 | 8/2002 | Corl et al. |
| 6,508,775 B2 * | 1/2003 | McKenzie et al. ............. 601/2 |

FOREIGN PATENT DOCUMENTS

WO    WO 00/18468    4/2000

* cited by examiner

*Primary Examiner*—Brian L. Casler
*Assistant Examiner*—William Jung
(74) *Attorney, Agent, or Firm*—Townsend and Townsend and Crew, LLP

(57) ABSTRACT

A therapeutic ultrasound delivery system, comprises: a catheter body, a plurality of axially spaced-apart hollow cylindrical vibrational transducers disposed along a length of the catheter body, a first spring connector wrapped around the outer surfaces of the vibrational transducers, where the first spring connector exerting an inward pre-stress on the outer surfaces of the vibrational transducers; and a second connector disposed in contact with the inner surfaces of the vibrational transducers. The second connector may comprise a spring coil, particularly a spring coil having multiple deflection points which contact an inner surface of the cylindrical vibrational transducer.

25 Claims, 18 Drawing Sheets

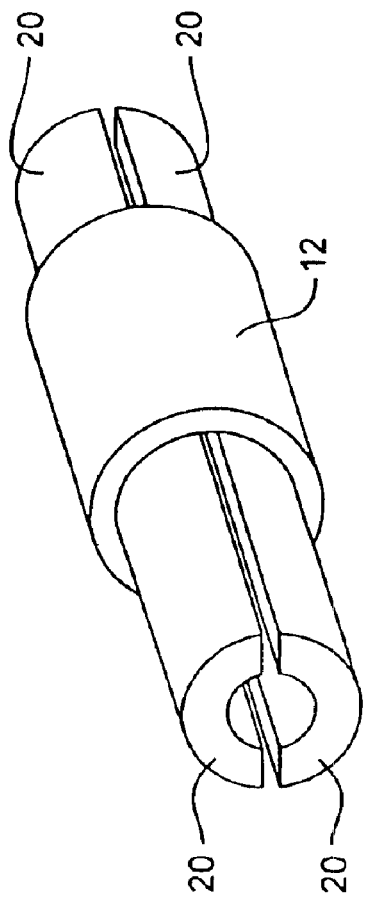
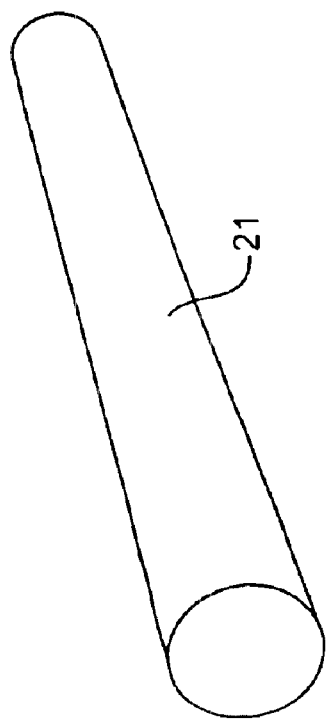
FIG. 8

HIGH OUTPUT THERAPEUTIC ULTRASOUND TRANSDUCER

CROSS-REFERENCES TO RELATED APPLICATIONS

The present application is a continuation-in-part of U.S. application Ser. No. 09/813,277, filed Mar. 20, 2001 now U.S. Pat. No. 6,508,775, which was a continuation-in-part of U.S. application Ser. No. 09/531,027 (U.S. Pat. No. 6,432,068 B1), filed Mar. 20, 2000, the full disclosures which are incorporated herein by reference in its entirety for all purposes.

BACKGROUND OF THE INVENTION

The present invention is related to medical devices and systems, particularly therapeutic ultrasound systems.

Percutaneously introduced catheters having ultrasound transducers thereon can be used to deliver localized doses of therapeutic ultrasound energy to various sites within a body. Such systems are ideally suited for treating or preventing pathological conditions such as arterial restenosis due to intimal hyperplasia.

To achieve a high level of therapeutic effectiveness, a high amplitude of ultrasound vibration is required. Unfortunately, the acoustic output from a conventional transducer design is typically limited by the inherent properties of the piezoelectric material which forms the transducer. Specifically, when operating typical piezoelectric ceramic transducers at high vibrational amplitudes, the ceramic tends to fracture. This transducer failure is caused by the high tensile stresses within the ceramic material during transducer operation, and the problem is exacerbated by the fact that although piezoelectric ceramic materials tend to have high compressive strengths, they have relatively low tensile strengths.

A further problem common to existing catheter-based ultrasound systems is that they lack the necessary flexibility to negotiate tortuous paths through body lumens. This is especially true when such systems comprise a plurality of axially spaced apart ultrasound transducers disposed along the length of the catheter body. In such cases, the catheter flexibility is unfortunately influenced both by the number and size of the conductors that are used to interconnect the various transducers.

A further problem common to existing catheter-based ultrasound systems which use a plurality of ultrasound transducers is the difficulty in individually wiring each of these transducers, since a large number of individual wires leading to each of the transducers typically results in a rather bulky system.

BRIEF SUMMARY OF THE INVENTION

The present invention provides ultrasound and other vibrational transducer systems comprising a vibrational transducer, typically an ultrasound transducer, which can be operated at very high vibrational amplitudes without failure. As such, the present invention provides systems to prevent the ultrasound transducer, which preferably comprises a ceramic piezoelectric material, from breaking apart at high amplitude operation. The present ultrasound transducer system is ideally suited for use in a catheter based therapeutic ultrasound energy delivery system.

In a preferred aspect, the present invention comprises a piezoelectric ceramic ultrasound transducer having a restraint received therearound. The restraint is dimensioned or otherwise formed to have a structure which exerts a compressive pre-stress on the piezoelectric ceramic transducer element where the stress can be maintained during the operation of the transducer. Advantageously, the compressive pre-stress provided by the restraint operates to prevent tensile failure of the ceramic transducer at high acoustic output.

In a preferred aspect, the strength of the compressive pre-stress provided by the restraint on the transducer is approximately equal to the tensile strength of the transducer element. As will be explained, when this occurs, the restrained transducer can provide approximately twice the acoustic output of a comparable un-restrained device before tensile failure occurs.

In one exemplary aspect, the strength of the compressive pre-stress provided by the restraint is approximately halfway between the tensile strength and the compressive strength of the ceramic transducer material. (Stated another way, the strength of the compressive pre-stress provided by the restraint is approximately equal to the average of the tensile strength and the compressive strength of the ceramic transducer material). As will be explained, when this occurs, the restrained transducer can be operated at a significantly increased output amplitude without failure.

In various preferred aspects, the compressive pre-stress provided by the restraint is just high enough to permit operation of the device without tensile failure at an output amplitude determined to be safe and effective for treating or preventing a pathological condition such as arterial restenosis due to intimal hyperplasia. In these preferred aspects, the required thickness and stiffness (as described below) of the restraint may be preferably kept to the minimum necessary to meet the acoustic output requirements, thereby minimizing the size of the device, and minimizing the requirements of the electrical drive circuitry, while maximizing the efficiency of the device in converting electric power into acoustic power.

In preferred aspects, the restraint may comprise a tensioned wire or filament(s) which is/are wrapped around the transducer. In other aspects, the restraint may comprise a jacket having an inner diameter which is initially fabricated to be slightly smaller than the outer diameter of the transducer. The jacket is then stretched to expand to a larger diameter such that it can just be received over the transducer. The transducer is then inserted within the expanded jacket, and the jacket is then allowed to contract such that it exerts a compressive pre-stress on the transducer. Systems for fabricating the jacket from a shape memory metal such as a nickel Titanium alloy (e.g.: Nitinol™) are also set forth.

The transducer is preferably cylindrically shaped, and may have an optional central longitudinal bore passing therethrough, with the bore defining an inner surface of the transducer. In various aspects, the inner and outer surfaces of the transducer are covered in whole or in part by an electrode. In alternative aspects, the opposite longitudinal ends of the transducer are covered in whole or in part by an electrode. In alternate embodiments of the invention, the transducer is formed from a series of alternating annular shaped polymer and piezoelectric ceramic rings, commonly referred to as a piezoelectric stack.

In a preferred aspect of the invention, the vibrational mode of the transducer is a relatively low frequency "breathing mode", wherein the circumference of the cylinder oscillates around a nominal value, and the stress within the ceramic is predominantly in the tangential direction. In this case, tensile stress from the vibration of the transducer which may otherwise lead to failure can be balanced by compressive pre-stress in the tangential direction applied by a wrapped jacket type restraint.

In an exemplary aspect, the transducer may be made of a PZT-8, (or PZT-4) ceramic material, but other piezoelectric ceramics, electro-strictive ceramic materials, or non-ceramic materials such as piezoelectric crystals may be used as well.

In the aspect of the invention in which a wrapped restraint is used, the tensioned member wrapped around the transducer may be a metal wire, metal or polymeric braid, mono-filament polymer, glass fiber, or a bundle of polymer, glass or carbon fibers. Wires may have circular cross sections or be formed as a ribbon or square wire. In various aspects, the wire is placed under tension when initially wrapped around the ultrasound transducer so as to maintain the compressive pre-stress on the transducer. Alternatively, the tension may be introduced after the wrapping is applied using thermal, chemical, mechanical or other type of process.

Suitable materials which may be used for either of the wrapped or jacket-type restraints described herein include, but are not limited to, high tensile strength elastic material selected from the group consisting of steel, titanium alloys, beryllium copper alloys, nickel, titanium and other shape memory allows (e.g.: Nitinol™), and epoxy impregnated kevlar, glass, polyester or carbon fiber. In one exemplary embodiment of the invention, the restraint comprises a 0.001"×0.003" Beryllium Copper alloy ribbon wire having a tensile strength of 150,000 psi or greater, wrapped around the transducer under 0.25 lbs of tension.

In aspects of the invention where the restraint comprises a wire or ribbon wire, the restraint may comprise multiple layers of wire or ribbon wrappings using thinner ribbon or smaller wire than would be used for a single layer of wrapped restraint. An advantage of using such smaller diameter wire or thinner ribbon wire would be that reduced bending stress would be experienced during the wrapping process, thereby permitting the wire or ribbon to be tensioned to a higher average stress without breaking. This in turn would allow a higher compressive pre-stress to be applied to the ceramic transducer element using a thinner and less stiff restraint than would instead be required for a single layer wrap of the same material.

In those aspects of the invention where the restraint comprises a wire, ribbon wire, or other fiber under tension, the wire restraint may be fixed in place on the surface of the transducer by gluing, soldering or welding, with the compressive pre-stress being maintained during the operation of the transducer. Such fixation could be continuous or only at spaced apart points or regions along the contact length between the restraint and the transducer.

The use of a beryllium copper alloy wire as the restraint has numerous advantages including its high tensile strength, (typically 150 kpsi or greater), corrosion resistance and conductive properties. A further advantage is that a beryllium copper alloy wire is easily solderable. As such, it may be soldered both to an outer surface of the transducer, and between adjacent wraps around the transducer without the need for a special solder tab. In addition, a beryllium copper alloy wire can easily be soldered at temperatures below the Curie temperature of the ceramic transducer material, (which is about 300° C. for PZT-8 ceramic). Typically as well, a beryllium copper alloy wire has a tensile strength/modulus of elasticity on the order of 190 kpsi/19Mpsi=$\frac{1}{100}$. This advantageous ration is similar to that of stainless steel which typically has a tensile strength / modulus of elasticity on the order of 300 kpsi/30Mpsi=$\frac{1}{100}$.

In the aspects of the invention where the restraint comprises a jacket, such jacket may be made from a very high strain limit material having good elastic properties and high tensile strength. Such a jacket could first be formed and then expanded to be slipped over the transducer and then allowed to recover, thereby radially compressing the transducer. If instead fabricated from Nitinol™, the jacket can be formed and then expanded to be slipped over the transducer. If maintained at a sufficiently low temperature, the jacket will maintain its expanded size as it is placed over the transducer. When the temperature is allowed to rise above a critical value the jacket material will contract, thereby applying compressive pre-stress to the transducer.

In preferred aspects, a composite polymer is applied over the outside of the restraint. The composite polymer is adapted to dampen longitudinal axis vibrations, to provide an electrical insulating layer and to provide a convenient surface to which an outer jacket of the catheter may be attached. Suitable materials for such a composite polymer include, but are not limited to, materials selected from the group consisting of high strength adhesives such as epoxy or cyano-acrylate, and polymers such as heat-shrinkable PVDF, polyester, nylon, Pebax, PVDF or polyethylene.

In preferred aspects, the ultrasound transducer is cylindrical in shape and may further comprise a longitudinally extending bore therethrough. When air is disposed within this bore, the ultrasound energy emitted by the transducer will be directed predominately radially outwards, since very little ultrasound energy passes from the dense ceramic transducer into the low density air. Thus, the efficiency of the transducer can be enhanced, providing an ideal transducer system for mounting on a catheter.

In various preferred aspects, a plurality of vibrational transducers are provided in the present catheter system. Preferably, such transducers are axially spaced apart along a length of the catheter body. In this plural transducer system aspect of the invention, the transducers preferably comprise hollow cylinders (i.e.: a cylinder having a longitudinally extending bore passing therethrough in an axial direction, as described above). These transducers preferably have inner and outer surfaces which are metallic and at which an electric voltage is applied, thereby driving transducer operation.

In accordance with the present invention, the restraint which may be wrapped or otherwise disposed around these transducers may comprise a continuous element extending over a plurality of successive transducers. Preferably, such a restraint extends over two, or more preferably three, or most preferably all of the axially spaced apart transducers in the probe or catheter.

In preferred aspects, such a restraint may comprise a flexible member which may comprise one or more wires or fibers having a spring or helix shaped or serpentine or zig-zag shaped structure.

In one preferred aspect, the restraint comprises a "spring connector" which is wrapped around (and extends over) a plurality of successive transducers, and exerts an inward compressive force on successive transducers.

As stated above, the preferred restraint may be wrapped around the outer surfaces of the successive axially spaced-apart transducers. Such a restraint exerts an inward pre-stress on the outer surfaces of the vibrational transducers such that transducer output can be increased, while simultaneously decreasing the likelihood of transducer failure. It is to be understood that reference herein to an outer "spring connector" is not limited, but is instead defined to include any form of flexible restraint which exerts an inward pre-loading on a plurality of axially spaced apart transducers.

In preferred aspects, the inward pre-stress exerted by the restraint received over the outer surfaces of the successive transducers is about 25% to 75% of the breaking (i.e. tensile) strength of the transducers.

The inward pre-stress exerted by the restraint (which may be wrapped or otherwise disposed around the outer surface of the transducers) may also be: (a) at least equal to the tensile strength of the transducers, (b) greater than the tensile strength of the transducers, and less than the average of the compressive and tensile strengths of the transducers (ie: ½ way between the compressive and tensile strengths of the transducers), or (c) approximately equal to the average of the compressive and tensile strengths of the transducers (ie: ½ way between the compressive and tensile strengths of the transducers).

It is to be understood that these ranges for the inward pre-stress exerted by the restraint wrapped or disposed around successive transducers will be most preferred when an inner connector, and may comprise a spring structure (which is received within the hollow bores of the successive transducers) exerts little or no appreciable outward pre-loading on the inner surfaces of the transducers. In preferred aspects, such an inner connector may comprise one or more wires or fibers having a spring or helix shaped or serpentine or zig-zag structure. In a most preferred aspect, the inner connector comprises a spring coil. Should the inner connector instead exert an outward pre-loading, the range of inward pre-loading exerted by the restraint can be increased accordingly to compensate.

While the spring coil or other inner connector will preferably exert little or no appreciable outward force on the inner surfaces of the transducer, it is still necessary that the conductor establish an adequate electrical contact with the transducer in order to power and operate the transducer. Thus, the spring coil or other inner connector should preferably apply a small radially outward force in order to maintain electrical contact. As the transducers become smaller, however, typically having inner passage diameters below 0.75 mm, often below 1.0 mm, the size of wire used for establishing the inner connection become smaller as well. Such smaller diameter wire, when wound into a coil, will be able to exert less outward radial force with the inner electrode surface, thus risking intermittent breaks in electrical contact. A preferred approach for enhancing electrical contact of spring coil inner connectors is to provide multiple deflection points in the wire prior to coiling. Such deflection points provide enhanced electrical contact with the inner surfaces of the vibrational transducers, greatly reducing or eliminating the risk of breaks in electrical contact.

Optionally, the restraint (which is wrapped around the outer surfaces of the transducers) can be attached to the outer surfaces of the transducers by a variety of techniques. These include, but are not limited to, gluing, soldering and welding. Alternatively, (or in addition to the foregoing attachment techniques) the restraint can be held in a fixed relation to the outer surfaces of the transducers by its natural tendency to contract or "re-coil" around the transducers. Specifically, the restraint may comprise a spring (or other shaped) connector which can be unwound such that it increases in diameter to the degree that it can be slipped over the transducers (while in its expanded state). Thereafter, the spring connector can be simply left to naturally "re-coil", such that it contracts around the outer surfaces of the transducers, and thereby exerts an inward pre-loading on the transducers. In this aspect, the natural (unexpanded) diameter of the spring connector is slightly smaller than the outer diameter of the transducers.

The use of the present restraint, which may comprise a spring connector disposed around the outer surface of the transducers offers many specific advantages, including, but not limited to, the following.

First, the natural tendency of the spring to contract operates to exert a desired inward pre-loading force on the transducers, thereby offering the advantages of increased output with reduced likelihood of transducer failure, as explained in reference to the various "restraints" described herein.

Secondly, a single spring connecting several transducers is very easy to install when the catheter system is first assembled. This is due to the fact that the wire spring simply be rotated at one end (while being held at its other end) to unwind it to a diameter sufficient that it can be slipped over the various transducers.

Thirdly, being a single continuous element which wraps around the outer surfaces of successive transducers, the present spring connector provides excellent ease and simplicity in system wiring as it can operate as a single electrical contact wire between the outer surfaces of the various transducers.

Fourthly, being a spring which preferably wraps rather firmly around the outer surfaces of the spaced-apart transducers, the present spring connector advantageously also holds the transducers apart at preferred axial separation distances, which remain constant over time.

In various preferred aspect of the invention, an inner connecting wire is disposed in contact with the inner surfaces of successive transducers. In a most preferred aspect, the inner connecting wire is a spring which is positioned in contact with the inner surfaces of the transducers. It is to be understood, however, that in accordance with the present invention, the inner connecting wire need not be in the form of a spring. For example, a simple wire (or wires) can be used to maintain electrical contact between the inner surfaces of successive transducers. However, in the preferred case where the inner connecting wire does comprise a spring, such a spring offers numerous advantages, including, but not limited to, the following.

First, a spring electrically connecting the inner surfaces of successive transducers to one another is very easy to install when the catheter system is first assembled. For example, such a wire spring may simply be rotated at one end (while being held at another) to tighten it to a diameter sufficiently small that it can be slipped within the hollow inner bore of successive transducers. After it has been so positioned, it is only necessary to release the wire such that it springs back (i.e.: expands) into a larger diameter state, (thereby gently pushing up against the inner surfaces of the transducers).

Secondly, being a single continuous element, such a spring connector provides excellent ease and simplicity in system wiring as can be operated as a single electrical contact wire connecting together the inner surfaces of the various transducers.

BRIEF DESCRIPTION OF THE DRAWINGS

FIG. 8 illustrates a tool for expanding a jacket such that it can be received over the transducer.

DETAILED DESCRIPTION OF THE INVENTION

A problem common to therapeutic ultrasound transducers is that when operating an ultrasound transducer such as a piezoelectric ceramic transducer at a very high output, the transducer will tend to fracture. Accordingly, the therapeutic effectiveness of catheter based ultrasound delivery systems have been somewhat limited since the level of vibrational amplitude of therapeutic ultrasound energy which their transducers are able to emit is limited, especially over prolonged periods of operation.

Figure 1:
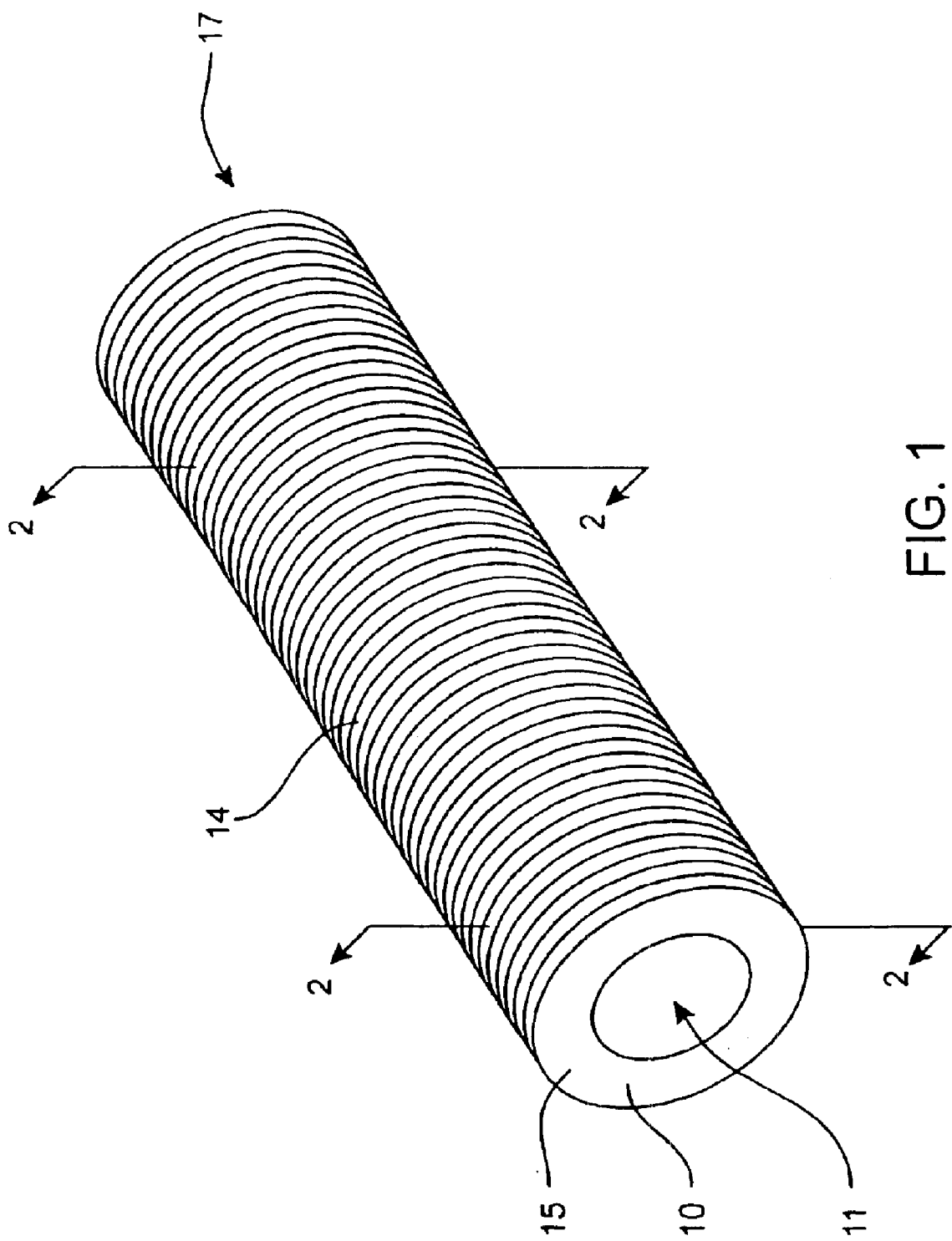
FIG. 1 is a perspective view of a cylindrical shaped ultrasound transducer having a wire restraint wrapped therearound.
Figure 2:
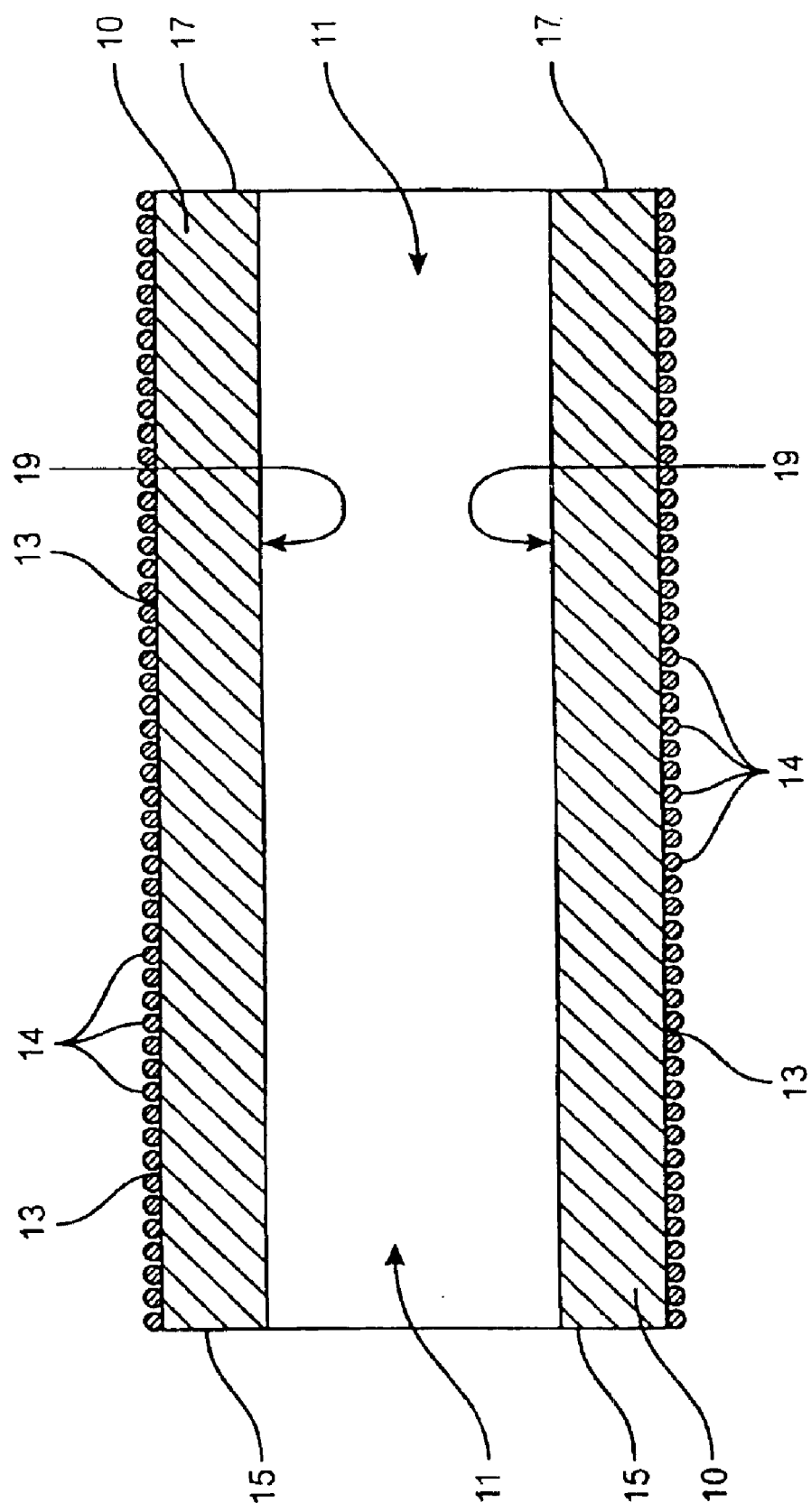
FIG. 2 is a sectional view taken along lines 2—2 in FIG. 1.

Referring to FIGS. 1 and 2, the present invention provides a system for preventing fracture of a ultrasound transducer, (such as a ceramic ultrasound transducer), when the transducer is operated at a high output. In a first aspect, the present invention provides a system for preventing tensile failure in a transducer 10, by way of a wire 14 which is wrapped tightly around transducer 10. As can be seen, transducer 10 is cylindrical shaped, having an optional longitudinally extending central bore 11 extending therethrough.

In various preferred embodiments, transducer 10 has a preferred outer diameter of 0.25 to 0.02 inches, a more preferred outer diameter of 0.175 to 0.03 inches, and a most preferred outer diameter of 0.100 to 0.03 inches.

In various preferred embodiments, transducer 10 has a preferred inner diameter of 0.2 to 0.01 inches, a more preferred inner diameter of 0.125 to 0.015 inches, and a most preferred inner diameter of 0.05 to 0.015 inches.

In various preferred embodiments, transducer 10 has a preferred length of 1.0 to 0.01 inches, a more preferred length of 0.750 to 0.010 inches, and a most preferred length of 0.5 to 0.01 inches.

It is to be understood, however, that the preferred dimensions set forth herein are merely exemplary and that the present invention is not so limited to the dimensions set forth herein.

In preferred aspects, the present system provides a "high output" of therapeutic ultrasound energy, being defined herein as being greater than that used for diagnostic imaging. In a most preferred aspect of the present invention, such "high output" is equal to or greater than 1.9 MI (mechanical index). In preferred aspects, the "high output" is achieved with an MI less than that at which cavitation damage occurs.

In preferred aspects, the present "high output" therapeutic ultrasound system is operated at an exemplary frequency range of equal to, or greater than, 500 KHz, and less than, or equal to, 3 MHz.

Preferably, wire 14 is pretensioned when initially wrapped around transducer 10 such that wire 14 exerts a compressive pre-stress on transducer 10. Wire 14 may be made of any suitable material selected from the group with mechanical properties exhibited by steel, titanium alloys, beryllium copper alloys, Nitinol™. Wire 14 may alternatively comprise a ribbon wire, or square wire, or a multi-strand wire. Wire 14 may alternatively comprise a high tensile strength elastic material such as epoxy-impregnated polyester, kevlar, glass or carbon fiber, in either a monofilament or multi-filament form.

In a preferred aspect, the tensile stress in wire 14 is about 100 kpsi or higher. In one exemplary aspect of the invention, the wire is a 0.001"×0.0003" Beryllium-Copper (BeCu) alloy ribbon wire under 0.3 lbs. tension, and transducer 10 is made of a PZT-8 ceramic having a 0.050" outer diameter, a 0.010" thickness wall, and a 0.315" length. In this exemplary aspect, the compressive pre-stress applied to the ceramic by the wrapped ribbon restraint is approximately 10 kpsi, which is comparable to the reported static tensile strength of PZT-8 ceramic at 11 kpsi, and significantly greater than the reported dynamic tensile strength of 5 kpsi.

Wire 14 is adapted to provide a compressive pre-stress on transducer 10, wherein the pre-stress is preferably maintained during the operation of transducer 10 by the resilience of the restraining wire.

In a preferred aspect, the compressive pre-stress exerted by wire 14 on transducer 10 is approximately equal to, or greater than, the tensile strength of the transducer. As will be explained, when the compressive pre-stress exerted on transducer 10 is approximately equal to the tensile strength of transducer 10, a doubling of output amplitude of transducer 10 is provided. In this preferred aspect of the invention, the stiffness of wire restraint 14 (or jacket 12) needed to provide this compressive pre-stress is only about ⅐ the stiffness of the transducer 10, therefore it does not appreciably restrain the motion of transducer 10, as follows.

The relationship between the stiffness of restraint 12 or 14 and the transducer 10 is established by considering that the modulus of elasticity "Y" of restraint 12 or 14 multiplied by the cross-sectional area of restraint 12 or 14, divided by the modulus of elasticity "Y" of transducer 10 multiplied by the cross-sectional area of transducer 10.

For example, using the BeCu ribbon at 19 Mpsi as wire 14, and PZT-8 ceramic as transducer 10, the modulus of elasticity "Y" of the BeCu ribbon is approximately 1.4 times the modulus of elasticity of the PZT-8 ceramic at 13 Mpsi, when the cross-sectional area of the BeCu ribbon is only about ⅒ that of the ceramic (1 ml ribbon thickness vs. 10 ml. transducer wall thickness). The relative stiffness of the restraint versus the transducer is then:

$$\frac{stiffness_{restraint}}{stiffness_{transducer}} = \frac{Y_{restraint} \cdot A_{rest}}{Y_{transducer} \cdot A_{transducer}} = \frac{19 \cdot 1}{13 \cdot 10} \approx \frac{1}{7}$$

In one exemplary aspect of the invention, the compressive pre-stress exerted by wire 14 on transducer 10 is approximately half-way between the compressive and tensile strengths of transducer 10, (e: at the average of the compressive and tensile strengths of transducer) thereby providing the highest possible output without failure, (as will be explained).

To ensure that wire 14 provides a compressive pre-stress on transducer 10, it is also important to ensure that wire 14 does not simply unwrap, thereby losing its contact from the outer surface 13 of transducer 10. Accordingly, wire 14 is preferably glued or soldered against outer surface 13 of transducer 10. Alternatively, adjacent wraps of wire 14 may be soldered, welded, or glued together with wire 14 being secured to the outer surface 13 of transducer 10 by friction.

In one embodiment, wire 14 is welded, soldered, or glued to transducer 10 or to adjacent wraps of wire 14 only at opposite transducer ends 15 and 17. An advantage of welding wire 14 only at ends 15 and 17 is that this avoids relieving the stress in wire 14 due to heating or melting. As such, a circumferential weld near each of ends 15 and 17 may be used to distribute the stress on the weld, with only a few turns of wire 14 near ends 15 and 17 being under reduced stress, with the (unheated) center turns of wire 14 exerting the compressive pre-stress on transducer 10. Alternatively, in another embodiment, wire 14 is welded or adhesively attached along the entire length of transducer 10 between ends 13 and 15.

Wire 14 may optionally be a ribbon wire, which has the advantage of distributing stress favorably over surface 13 of transducer 10, with the entire width of the ribbon in contact with the ceramic transducer 10, instead of just a narrow strip where a round wire would be in tangential contact with the cylindrical transducer surface. Furthermore, since a ribbon wire provides the maximum amount of metal in a minimum profile, a ribbon wire permits the maximum restraint with minimum increase in the overall dimension of the restrained transducer. Furthermore, due to its narrow dimension in the radial direction, ribbon wire would experience much lower bending strain during the wrapping process as compared a round wire of comparable cross-sectional area per unit length. Another advantage of ribbon wire is that it is resistant to stress relief during the welding process in which wire 14 is attached to outer surface 13, since the actual weld would only occupy a portion of the ribbon width leaving a large remaining portion to sustain tensile stress while the welding takes place.

In preferred aspects, wire 14 is selected from a material with an elongation at failure of greater than wire diameter/transducer radius, having the highest possible tensile strength. Alternatively, ribbon wire 14 is selected from a material with elongation at failure of greater than wire thickness/transducer radius, having the highest possible tensile strength. In either case, the lowest possible modulus is desired so that there is a minimum of restraint exerted on transducer 10. Examples of such materials include Beryllium Copper (BeCu) alloy 172, with various tempers having tensile strengths of 100–240 kpsi and elongation of 1–10%, or various stainless steel alloys, or high strength Titanium alloys.

In a preferred aspect, wire 14 is wrapped over itself such that a multi-layer restraint is provided. An advantage of wrapping smaller diameter wire is that it will exhibit a lower bending stress, as compared to a larger diameter wire wrapped around the transducer.

In one preferred aspect, opposite ends 15 and 17 of transducer 10 may be electroded. Alternatively, in another preferred aspect, an inner surface 19 and outer surface 13 may instead be electroded.

Figure 3:
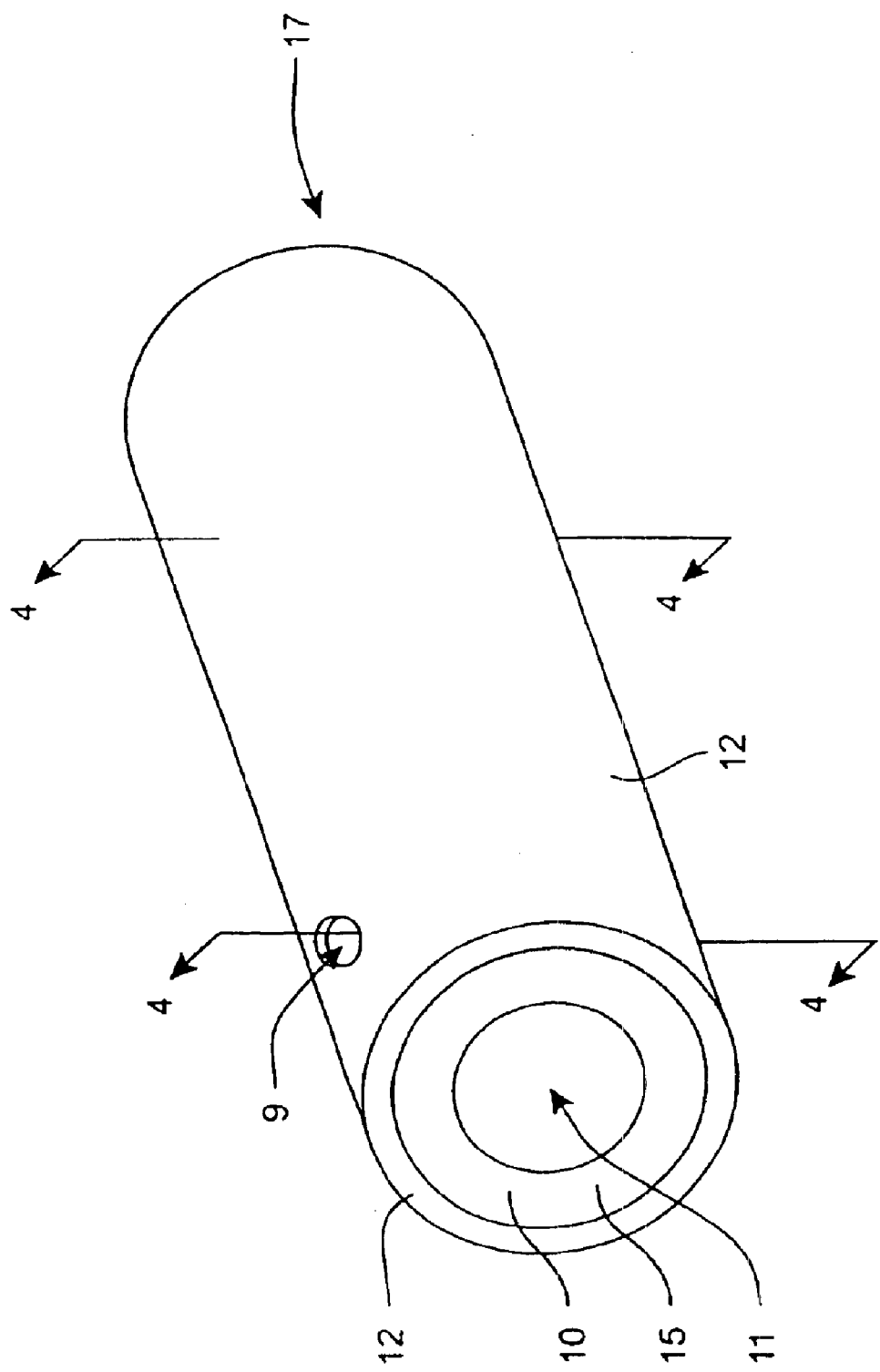
FIG. 3 is a perspective view of a cylindrical shaped ultrasound transducer having a restraining jacket received thereover.
Figure 4:
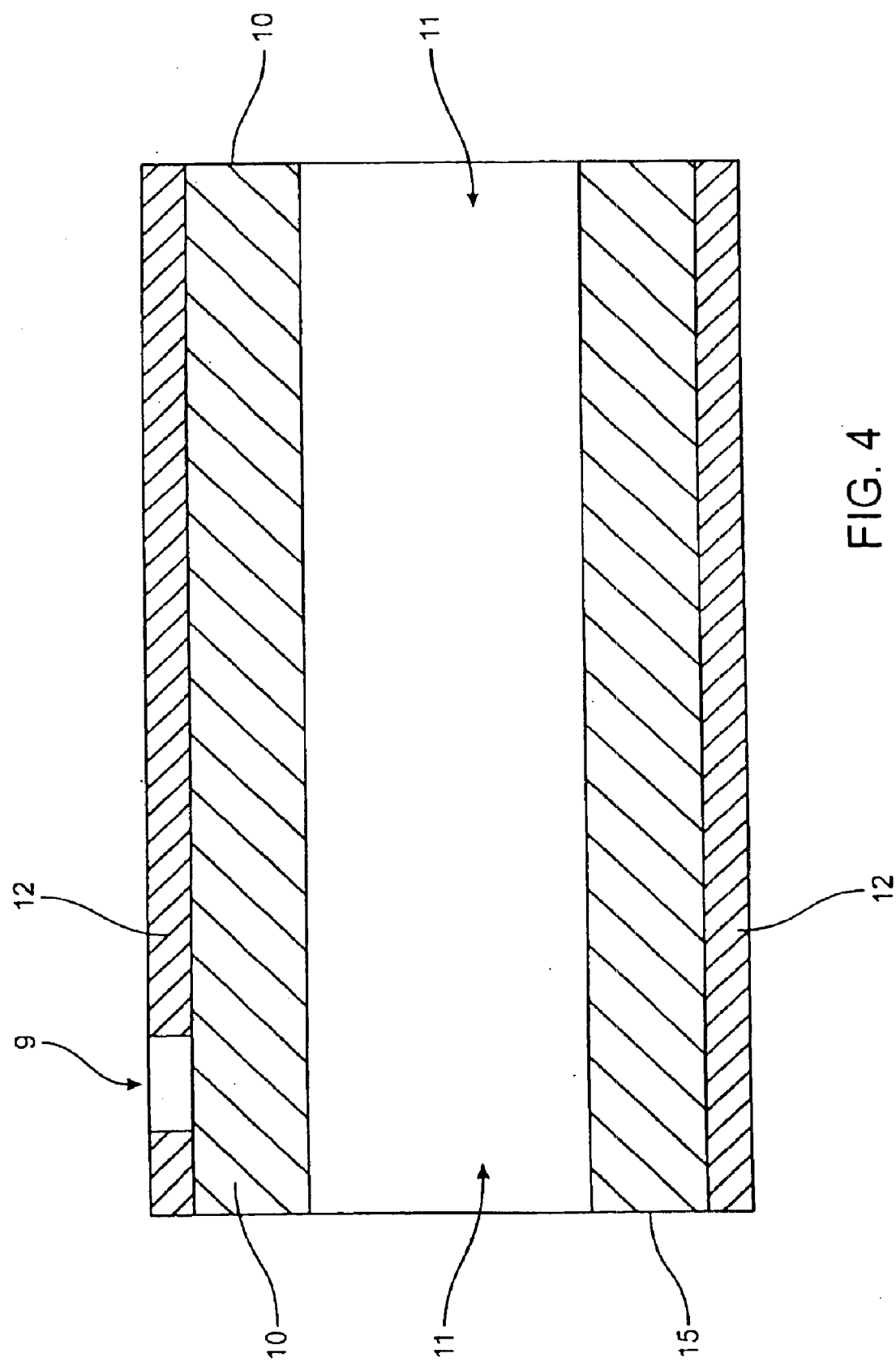
FIG. 4 is a sectional view taken along lines 4—4 in FIG. 3.

In an alternate embodiment of the invention, the restraint used to exert a compressive pre-stress on the transducer comprises a jacket received over the transducer. Referring to FIGS. 3 and 4, transducer 10 is shown surrounded by a restraint jacket 12 which is slipped thereover and exerts a compressive pre-stress, similar to that exerted by wire 14, as was described above.

Jacket 12 may preferably be formed to maintain a compressive pre-stress on transducer 10 in a number of ways. In a first aspect, jacket 12 is initially formed with an inner diameter slightly less than the outer diameter of transducer 10. Thereafter, jacket 12 is stretched radially by mechanical or thermal means to expand its inner diameter to a dimension such that it can just be slipped over transducer 10, with transducer 10 received therein as shown in FIGS. 3 and 4. After jacket 12 has been slipped over transducer 10, jacket 12 will then be released such that it naturally contracts somewhat around outer surface 13 of transducer 10. Consequently, jacket 12 exerts, and maintains, a compressive pre-stress on transducer 10 during its operation.

Jacket 12 may preferably be fabricated from a high tensile strength elastic material, including any of the exemplary materials set forth above with respect to wire 14. Alternatively, jacket 12 may be fabricated from a shape memory metal such as Nitinol™. In this aspect of the invention, a change in temperature will alter the size of jacket 12 such that it constricts around transducer 10 after having been received thereover. For example, a Nitinol™ alloy can be chosen to be Martensitic at the temperature of liquid nitrogen, and super-elastic in the temperature range from room temperature to body temperature and slightly above. The Nitinol™ alloy would be austenitic at elevated temperatures. Such a material can be fabricated as a thin wall tube with inner diameter slightly less than that of the transducer. For example, the ceramic transducer could have an outer diameter of 0.050" with a 0.010" wall thickness and a 0.315" length. The Nitinol™ tube could be fabricated with an inner diameter of 0.048" and a wall thickness of 0.002". When the Nitinol™ is cooled to liquid nitrogen temperature (~200° C.) the Nitinol™ becomes Martensitic and is relatively easily expanded to an inner diameter of 0.052", allowing it to be slipped over the outside of the ceramic transducer. When the Nitinol™ warms up to room temperature, it becomes super-elastic, and it attempts to recover to its original fabricated dimensions. The recovery is limited by the ceramic, but the super-elastic alloy applies a compressive pre-stress to the ceramic, thereby preventing premature tensile failure of the ceramic.

When using either jacket 12 or wire 14 as the restraint on transducer 10, such restraint will preferably have a high tensile strength so that only a thin layer of the restraint material will be adequate, yet also have to have a low stiffness such that it would not unduly restrain the ceramic transducer 10.

Figure 5:
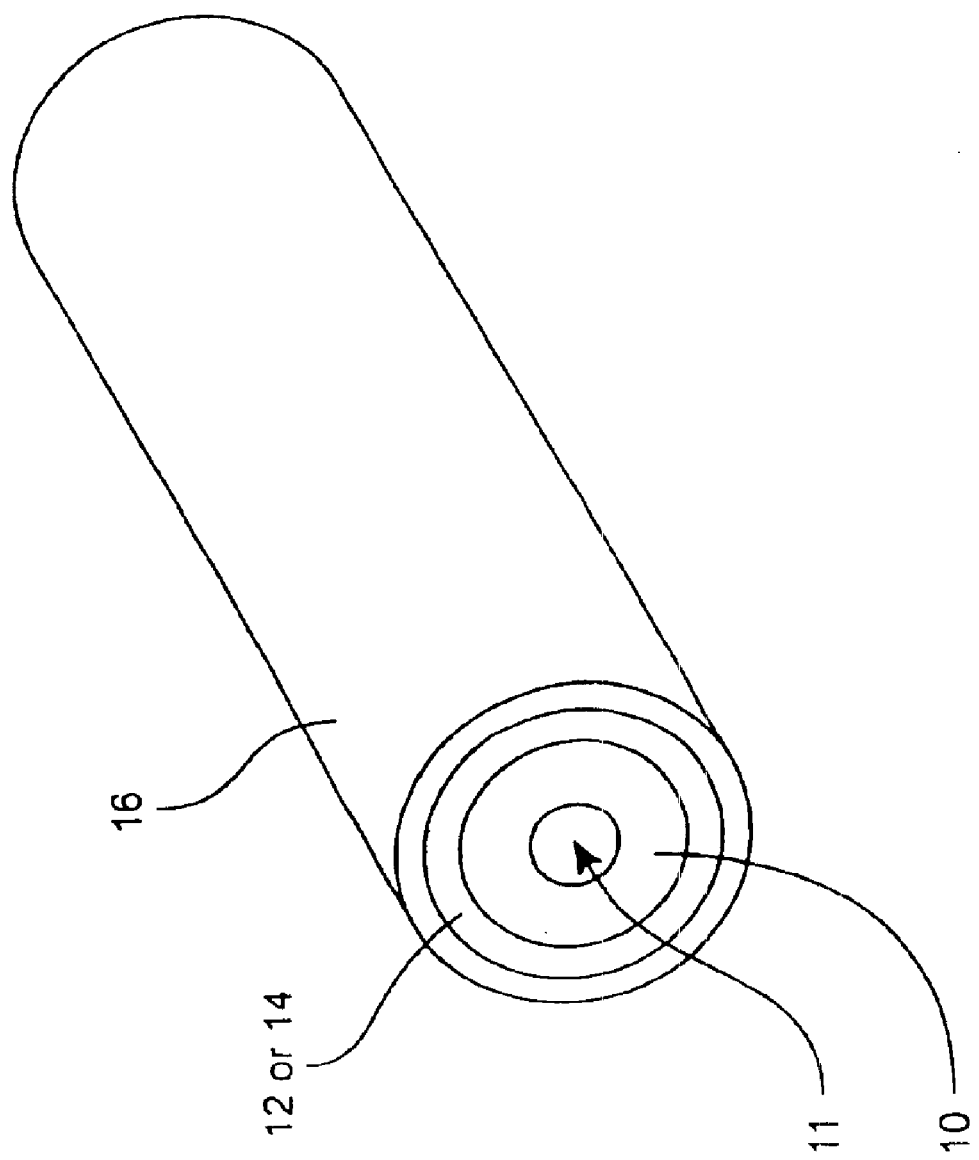
FIG. 5 is a perspective view of a transducer and restraint received within an outer coating.

When using either a wire restraint (FIGS. 1 and 2) or a jacket restraint (FIGS. 3 and 4), the restraint is preferably received within an outer coating 16, as shown in FIG. 5. Outer coating 16 may preferably comprise a composite polymer, which operates to dampen longitudinal vibrations and provide an electrical insulating layer. In an exemplary aspect, outer coating 16 comprises a high strength thin wall polymer such as 0.001" thick polyester or nylon polymer, attached to jacket 12 by a high strength adhesive, preferably having at least 500 psi shear strength.

Figure 6:
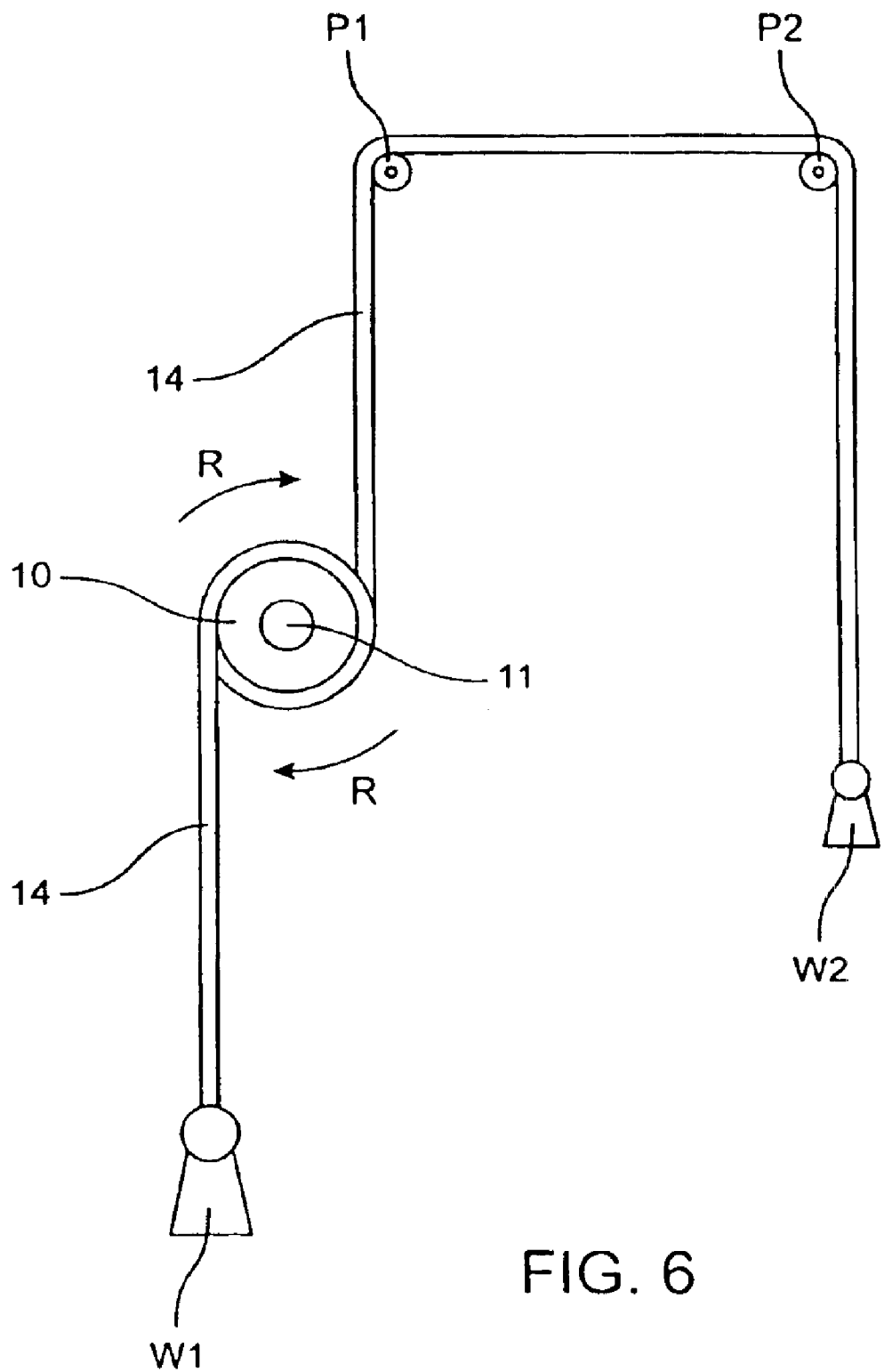
FIG. 6 is an illustration of a system for wrapping a tensioned wire around an ultrasound transducer.

The present invention also sets forth systems for wrapping wire 14 around transducer 10 such that wire 14 remains in tension. Referring to FIG. 6, two strands of wire 14 are shown being wrapped simultaneously around transducer 10 as transducer 10 is rotated in direction R. In this system, a pair of equal weights W1 and W2 keep wire 14 under tension as wire 14 passes over pulleys P1 and P2. Since W1 and W2 are equal, the wires 14 will not produce any net bending stress on the transducer 10 which could cause it to break during the manufacturing process. Alternatively, weight W2, pulleys P1 and P2 and one wire 14 may be eliminated to simplify the wrapping fixture. In this case, the transducer 10 must be strong enough to resist the bending stress created by the tensioned wrapping wire 14.

Longitudinally extending bore 11, as seen in FIGS. 1 to 5, may preferably be air filled. Advantages of an air-filled bore include the fact that ultrasound energy can not be transmitted thereacross. Instead, all of the ultrasound energy emitted by transducer 10 will advantageously be reflected off of inner surface 19, and directed radially outwardly, thereby increasing the therapeutic effectiveness of transducer 10. Another advantage of air-filled bore 11 is that it can be used for passage of a guidewire therethrough.

Figure 7A:
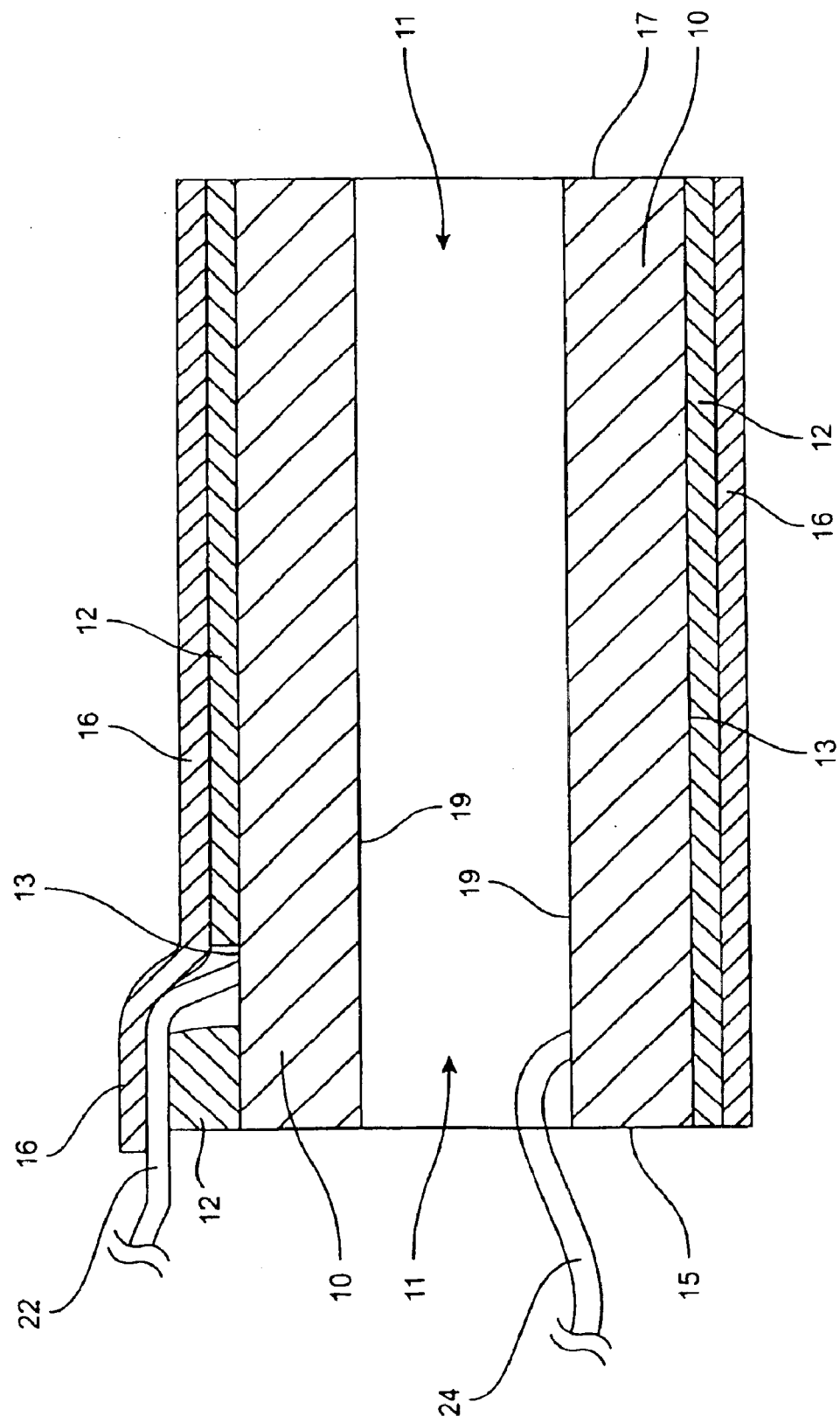
FIG. 7A is a sectional view corresponding to FIG. 5, showing electrodes attached to inner and outer surfaces of the transducer, with the restraining jacket as shown in FIGS. 3 and 4.
Figure 7B:
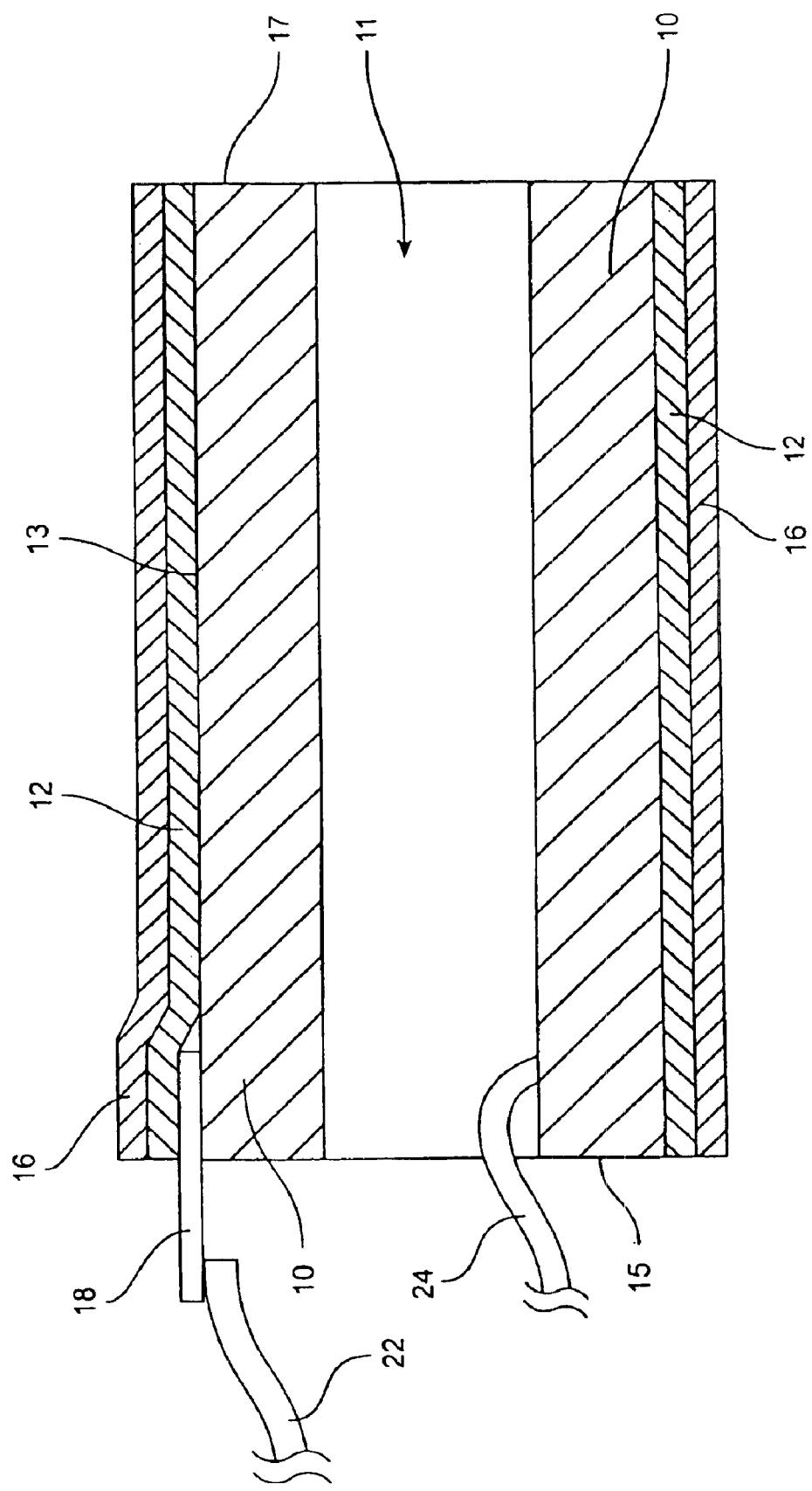
FIG. 7B corresponds to FIG. 7A, but instead shows an electrode connected to the outer surface of the transducer by way of a solder tab.
Figure 7C:
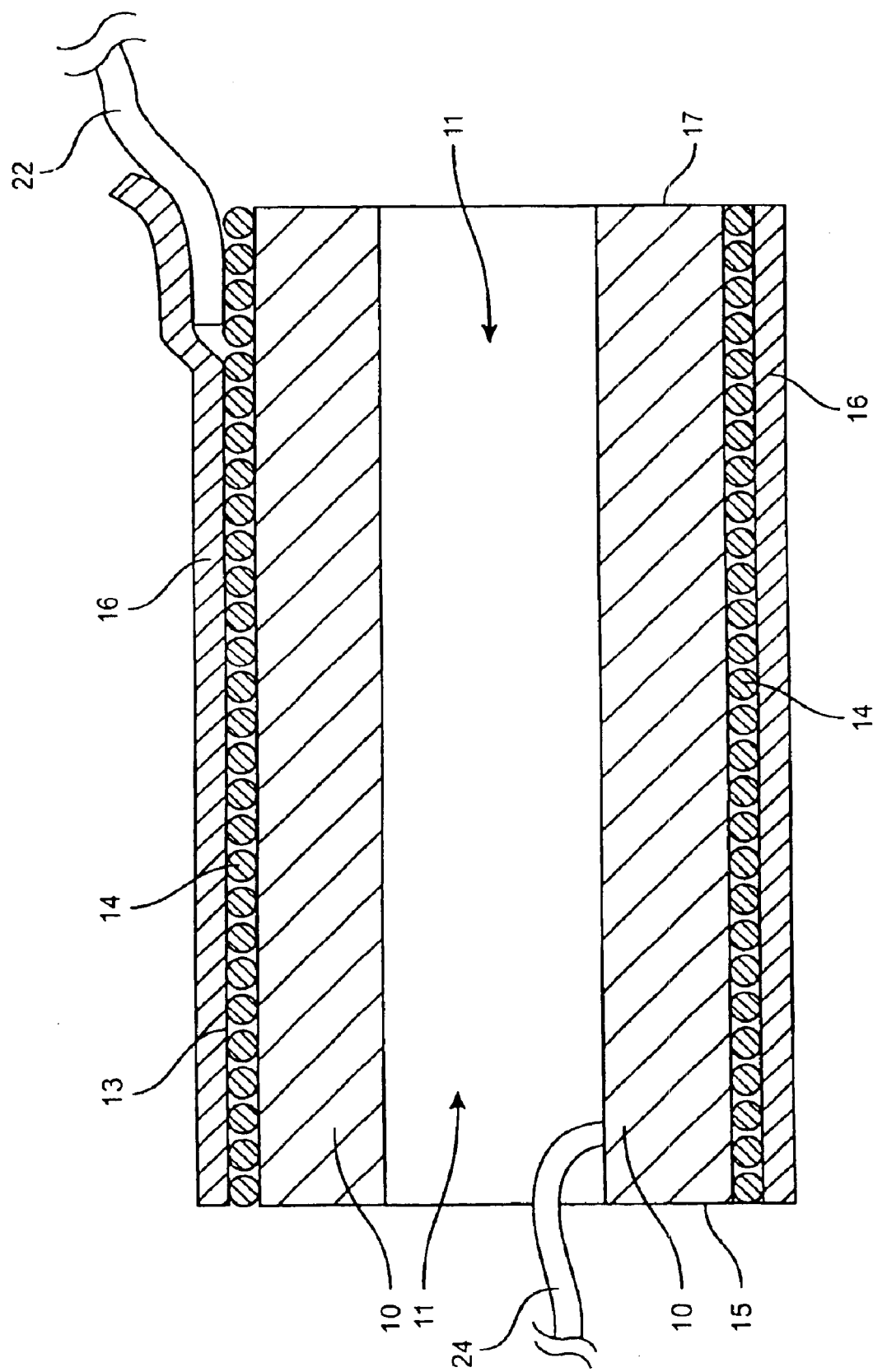
FIG. 7C corresponds to FIG. 5, but instead shows an electrode soldered directly to the restraining wire, as illustrated in FIGS. 1 and 2.

FIG. 7A shows an embodiment of the present invention in which jacket 12 is made of Nitinol™, with an electrical lead 22 passing under outer covering 16 and through a hole 9 passing through jacket 12 such that an electrical lead 22 may be attached to electroded outer surface 13 of transducer 10. Similarly, an electrical lead 24 is attached to the inner surface 19 of transducer 10 as shown. FIG. 7B shows electrical lead 22 connected to electroded outer surface 13 by way of a solder tab 18. FIG. 7C shows electrical lead 22 soldered directly to electrically conductive wire 14, which is in direct contact with electroded outer surface 13 of transducer 10.

In a preferred aspect, wire 14 is soldered at ends 15 and 17 to prevent unwrapping from transducer 10. The outer electrode connection may be made by soldering directly to wire 14. As such, transducer 10 can be wrapped all the way from end-to-end with no unwrapped segment required for lead attachment.

FIG. 8 illustrates a tool for expanding jacket 12 such that it can be received over transducer 10. The tool comprises a split mandrel 20 and a tapered conical wedge 21. Conical wedge 21 is inserted into a bore passing through split mandrel 20 such that jacket 12 can be expanded. In a preferred aspect, jacket 12 is made of Nitinol™, and the insertion of wedge 21 into mandrel 20 is preferably done at a cool temperature such that when Nitinol™ jacket 12 returns to a warmer temperature, it will tend to retract radially inwards. In an exemplary aspect, Nitinol™ jacket 12 will have a thickness of approximately 0.002", offering an improved compromise in terms of strength and low restraint.

In preferred aspects, transducer 10 will be operated at a low temperature rise. Such low temperature rise can be achieved by maintaining a low duty cycle, or alternatively by providing a cooling flow such as a saline infusion over transducer 10 during its operation. Preferably, a temperature rise of less than 5° C. will be achieved. Preferably, the fluid could be introduced through an annular space between transducer 10 and a polyimide guidewire sleeve. Temperature monitoring by a catheter mounted thermistor or thermocouple can also be used.

Figure 9:
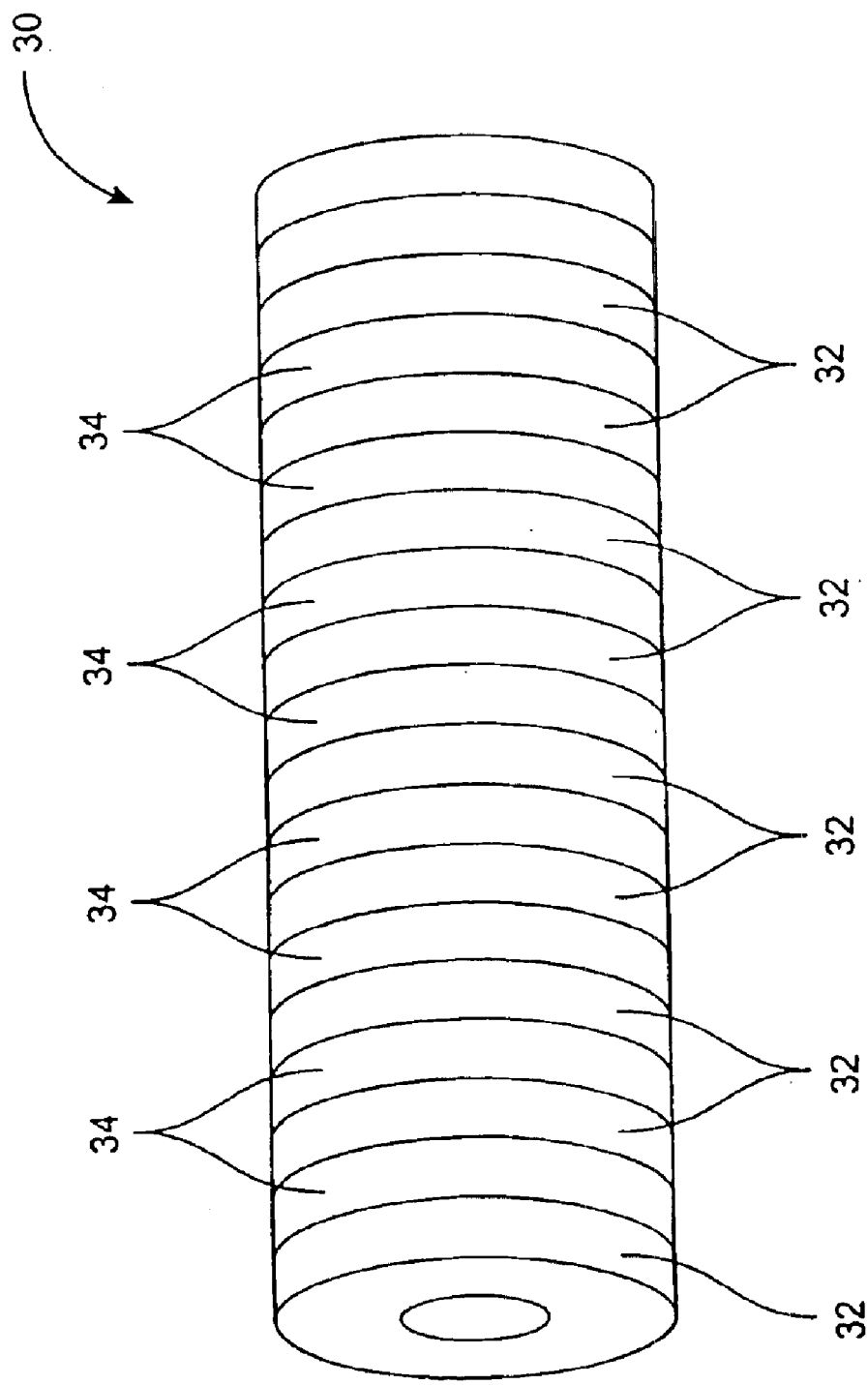
FIG. 9 shows an alternate ultrasound transducer comprising alternating annular piezoelectric and polymer sections.

Referring to FIG. 9, an alternate transducer system is provided with transducer 30 comprising alternating annular sections of PZT ceramic 32 and polymer 34. Transducer 30 is ideally suited to avoiding longitudinal failure. In accordance with the present invention, transducer 30 may be substituted for transducer 10 in any of the above described embodiments of the present invention. For example, transducer 30 is preferably restrained by a wire 14 wrapped therearound, or a jacket 12 slipped thereover, the restraint used in turn being received within outer covering 16, as described.

As stated above, the strength of the compressive pre-stress provided by wire 14 or jacket 12 on transducer 10 is at least approximately equal to the tensile strength of the transducer material and more preferably, approximately equal to the average of the tensile and compressive strengths of the material. (ie: at a value ½ way between the tensile and compressive strengths of the material). This is explained as follows.

Figure 10:
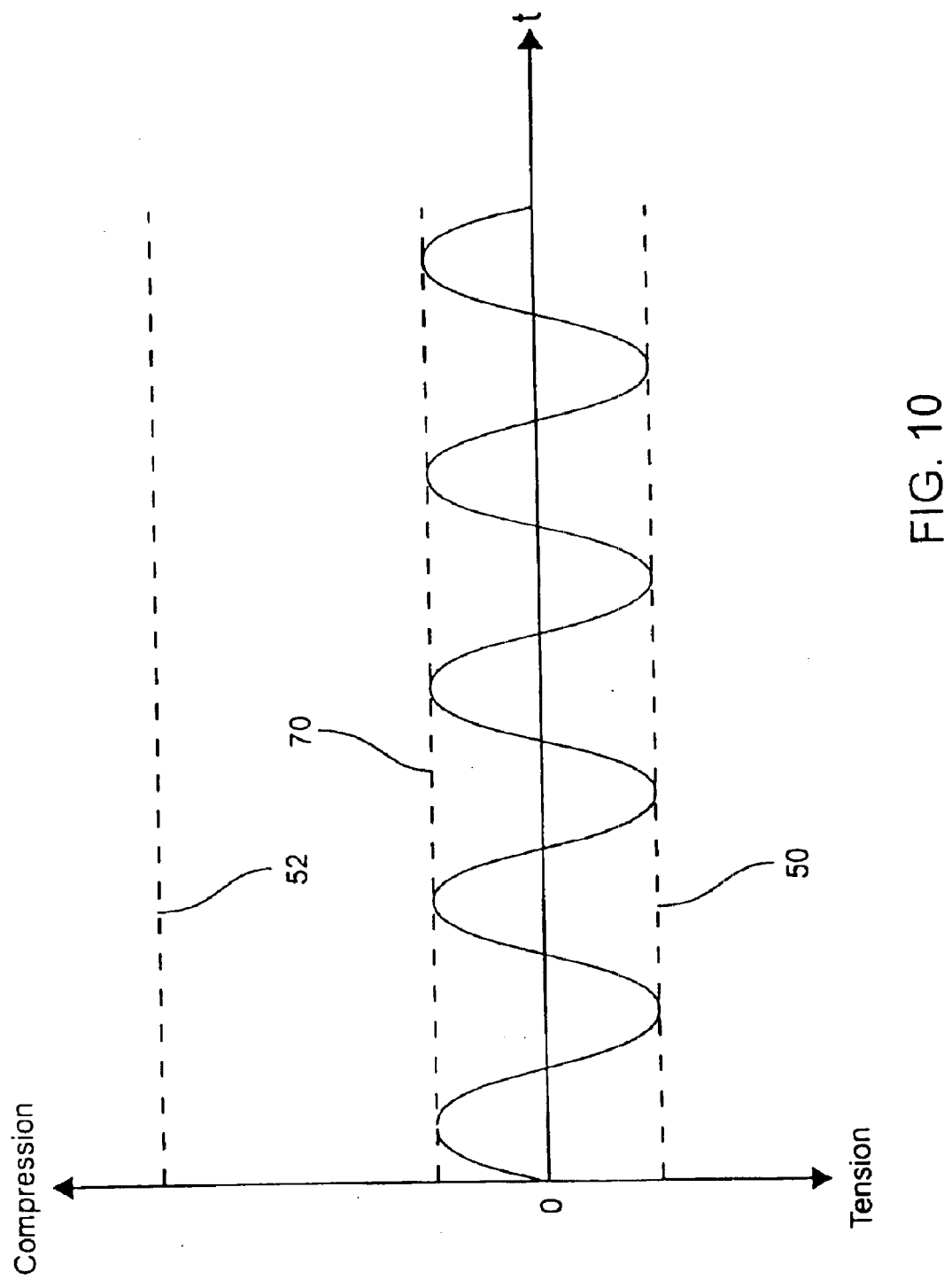
FIG. 10 shows a stress vs. time plot for an unrestrained transducer.

Referring to FIG. 10, a stress vs. time plot for an unrestrained transducer is shown. Acoustic vibrations in the transducer are characterized by oscillation in the stress. In a conventional transducer, without a pre-stress, the stress oscillates around zero, alternating between compressive (positive) stress and tensile (negative) stress.

Since piezo-electric ceramic materials typically have much higher compressive strengths compared to their tensile strengths, compressive pre-stress permits higher acoustic amplitude without subjecting the ceramic to tensile stress beyond its limit. Specifically, the tensile strength of the transducer material is shown by line 50 and the compressive strength of the transducer material is shown by line 52. (As can be seen, line 50 is closer to zero than line 52, thus indicating that the transducer is more likely to fail in tension than in compression). If the stress during one of the cycles of oscillation exceeds the tensile strength of the ceramic, then the transducer will fracture. Accordingly, when operating an unrestrained transducer, the maximum tensile stresses will equal the maximum compressive stresses. Accordingly, the maximum peak-to-peak amplitude of the oscillations in the stress (i.e.: the difference between lines 50 and 70) will be double the tensile strength (i.e.: the difference between zero and line 50) of the transducer material.

Figure 11:
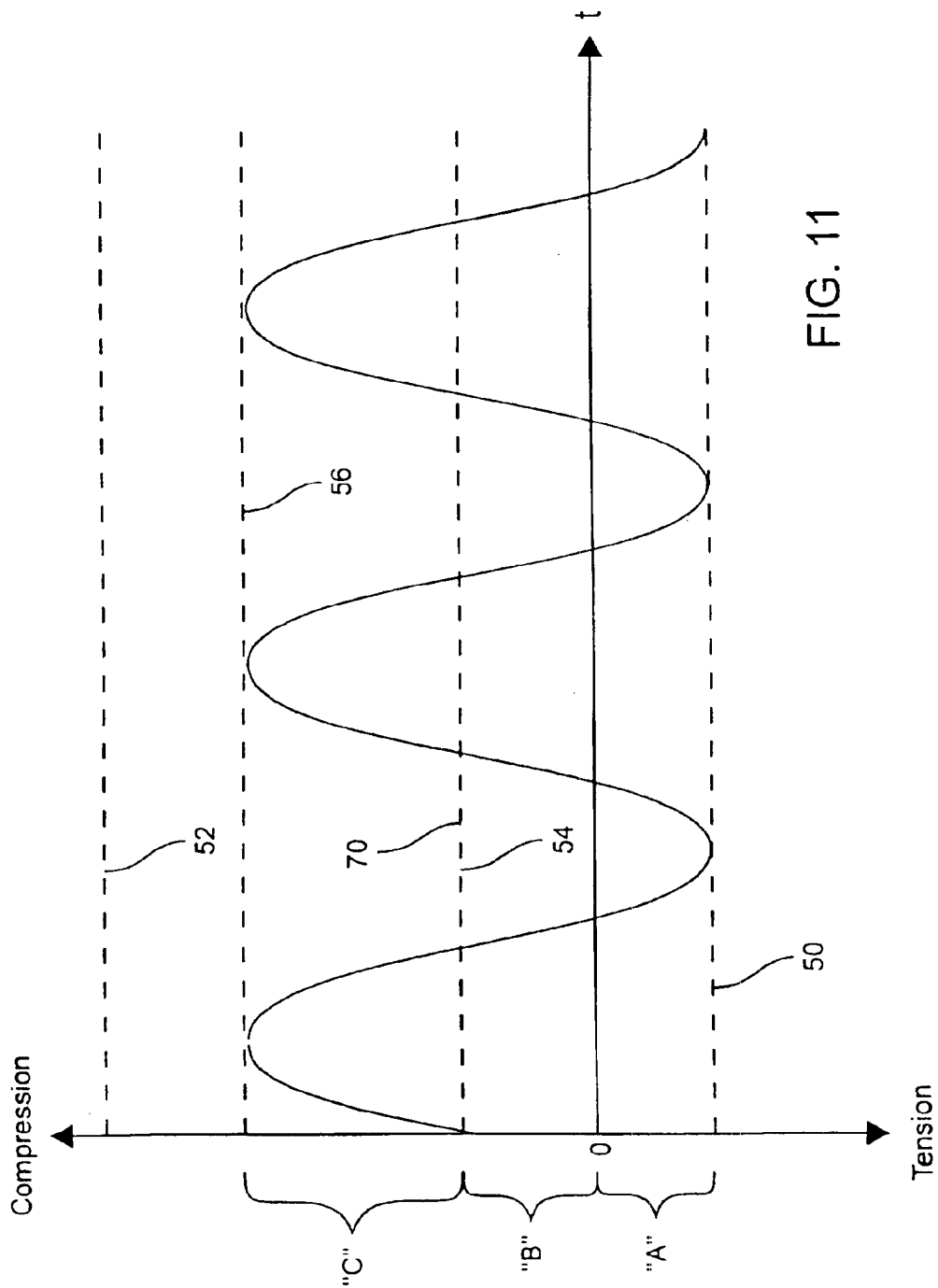
FIG. 11 shows a stress vs. time plot for a restrained transducer, operating at less than optimal output.

FIG. 11 shows a stress vs. time plot for a transducer with a restraint wrapped therearound. In this aspect of the invention, the compressive pre-stress (labeled as distance "B"), (ie: the difference between zero and line 54) is equal to the tensile strength (labeled as distance "A"), (i.e.: the difference between zero and line 50) of the transducer material. Thus, line 54 is at the same level as line 70. As can be seen, the application of such a compressive pre-stress to the transducer results in a doubling of the maximum peak-to-peak amplitude of oscillation in the stress relative to that of a comparable unrestrained transducer, (i.e.: the difference between line 56 and zero is twice the difference between line 54 and zero).

Figure 12:
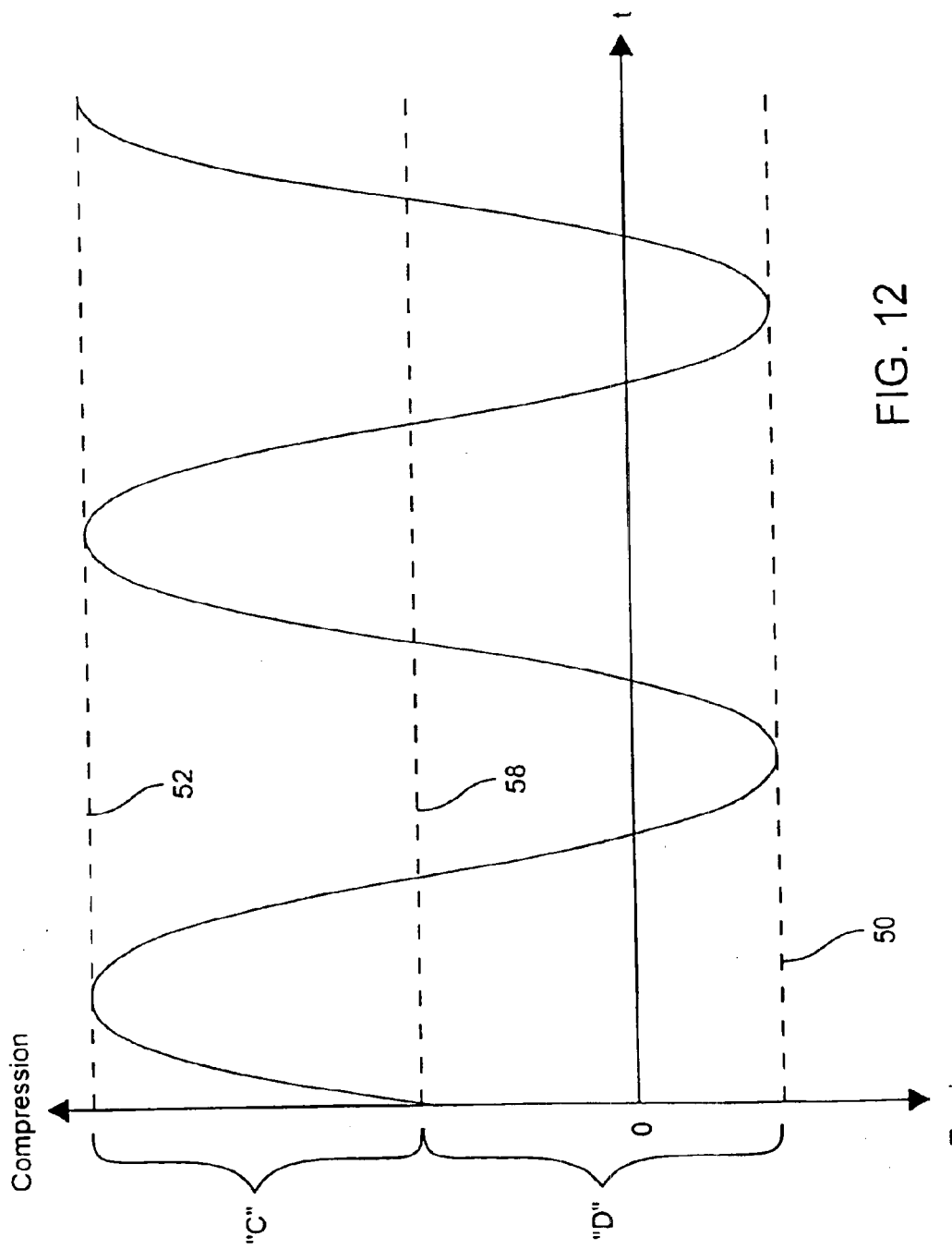
FIG. 12 shows a stress vs. time plot for a restrained transducer, operating at optimal output.

FIG. 12 shows a stress vs. time plot for a transducer with a restraint wrapped therearound, operating at optimal output. In this aspect of the invention, the compressive pre-stress applied by the restraint (line 58) is set to be positioned at an average (ie: ½ way between) the tensile strength (line 50) and the compressive strength (line 52) of the transducer material. As can be seen, the application of such a compressive pre-stress on the transducer effectively maximizes the peak-to-peak amplitude of the oscillation in the stress to a level corresponding to the difference between compressive strength (line 52) and the tensile strength (line 50).

Accordingly, in preferred aspects of the invention, the compressive pre-stress applied to the transducer by the restraint is at least equal to, and preferably greater than, the tensile strength of the transducer. More preferably, the compressive pre-stress applied to the transducer by the restraint is of an amplitude greater than the tensile strength of the material and not exceeding an average value (ie: a value ½ way between) the tensile and compressive strengths of the material. In an optimal aspect of the invention, the compressive pre-stress is equal to the average of the tensile and compressive strengths of the material.

In another preferred aspect of the invention, the compressive pre-stress applied to the transducer is sufficient to permit reliable operation at the desired acoustic output amplitude, without permitting tensile failure of the ceramic and without requiring an unnecessarily stiff or bulky restraint.

As such, FIGS. 11 and 12 provide illustrations of how compressive pre-stress permits higher amplitude acoustic vibrations without stress exceeding the tensile strength limit of the ceramic compressive strength of ceramic.

Figure 13:
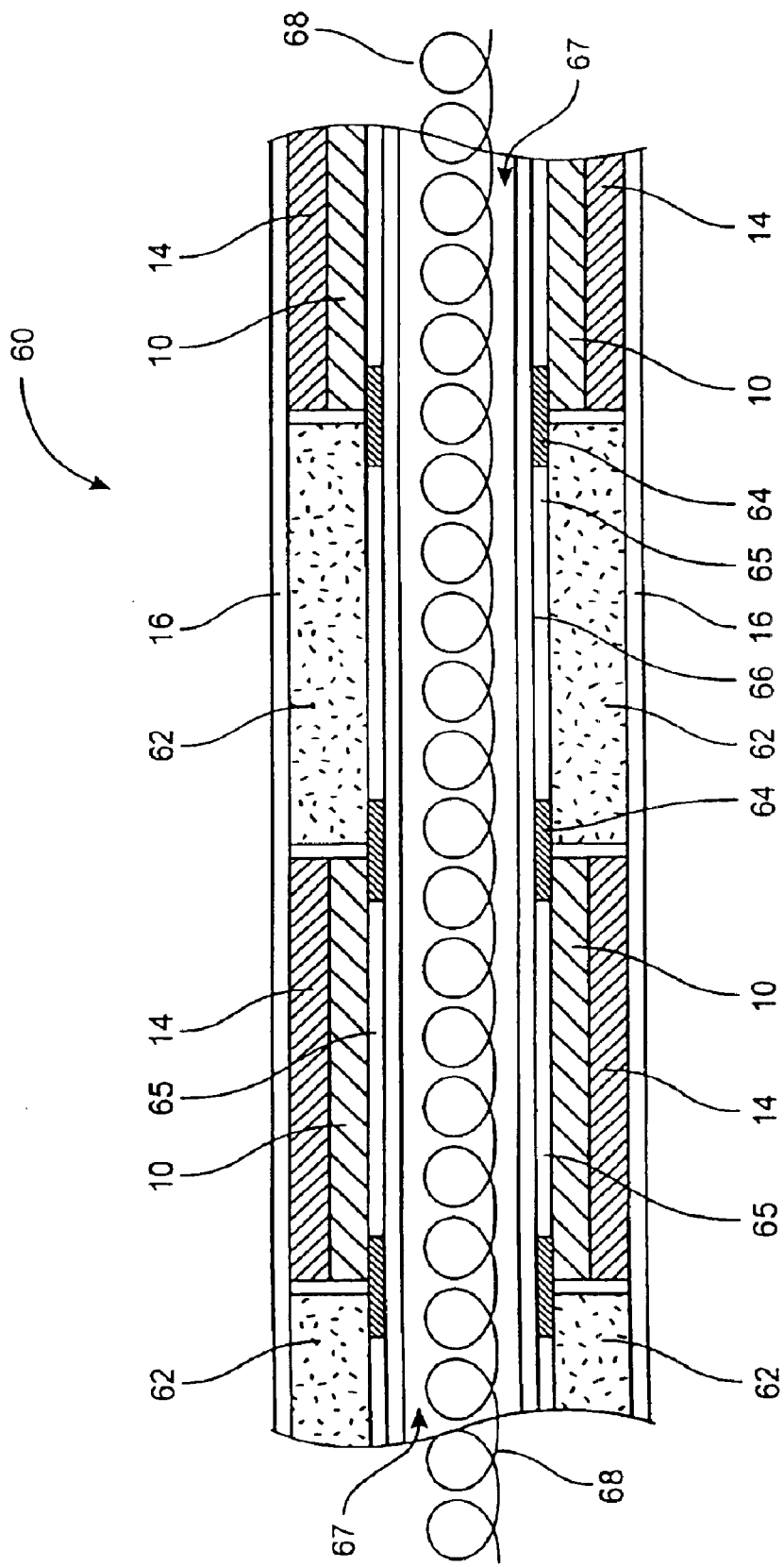
FIG. 13 shows a plurality of the present transducers mounted to a catheter system for delivering therapeutic ultrasound to a patient.

Lastly, FIG. 13 is an illustration of a plurality of the present cylindrically shaped high output ultrasound transducers 10, with wrapped wire restraint 14 thereover, as previously described herein, mounted along a flexible catheter 60 with spacers 62 disposed therebetween. Spacers 62 may be formed from a flexible polymer material so as to permit catheter 60 to flex between the rigid transducer (10) segments. Outer covering 16 may preferably be formed from a flexible polymer which bonds to jacket 12, and provides a smooth outer surface for catheter 16. A plurality of optional bushings 64 are disposed between transducers 10 and spacers 62, forming an air gap 65 adjacent the inner surface 66 defining lumen 67 through which guide wire 68 passes, as shown. In a preferred aspect, the guidewire lumen 67 is lubricious and flexible and contains guidewire 68 and has a fluid (such as saline) passing therethrough to provide cooling for transducers 10. Air gap 65 operates to direct the ultrasound energy emitted by transducers 10 radially outwardly, by inhibiting radially inward ultrasound emissions. A preferred material for guidewire lumen 67 is high density polyethylene.

FIGS. 14 to 17 show an aspect of the invention in which a plurality of axially spaced-apart transducers are used, with coiled springs wrapped around their inner and outer surfaces. As explained herein with reference to other embodiments, the present invention can be used to provide therapeutic ultrasound delivery to a patient. It is to be understood that although the structure of the outer restraint as illustrated herein is that of a "spring connector", the present invention is not so limited. Rather, other shapes of connectors can be used, including serpentine, zig-zag and various helical structures, all keeping within the scope of the present invention.

Figure 16:
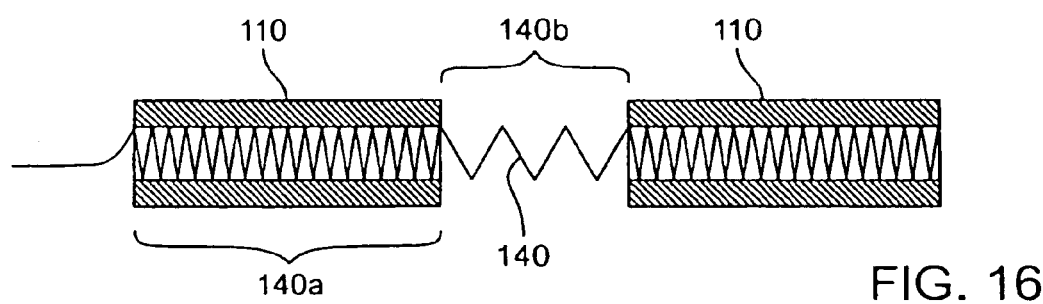
FIG. 16 is an illustration similar to FIG. 14, but showing more coils per unit distance within each transducer than between successive transducers.
Figure 17:
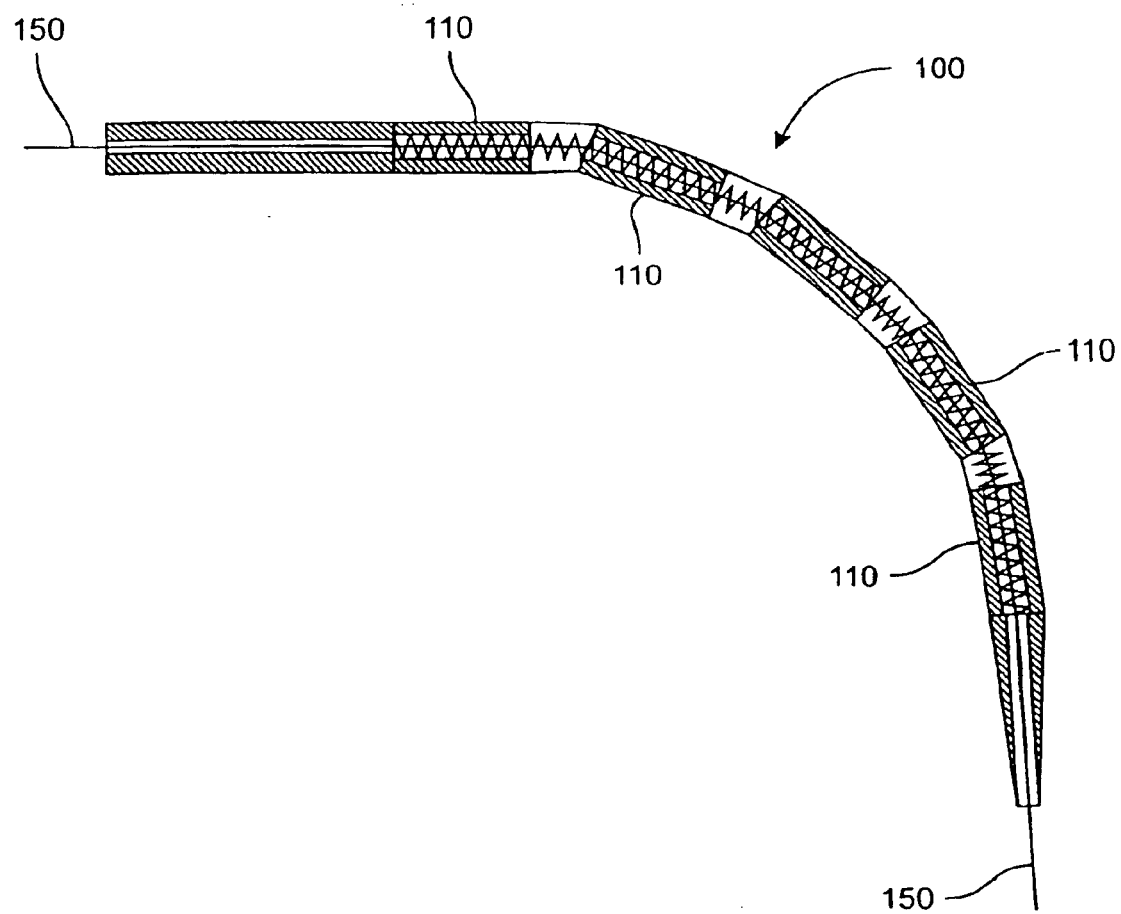
FIG. 17 is an illustration of an ultrasound catheter system according to the present invention, showing the flexibility of the present system.

Referring first to FIG. 17, a catheter 100 having a plurality of hollow cylindrical ultrasound transducers 110 which are spaced apart in an axial direction along the length of the catheter body is shown. Close-up views of successive transducers 110 are shown in FIGS. 14 to 16 (with the catheter body removed for ease of illustration).

Figure 15:
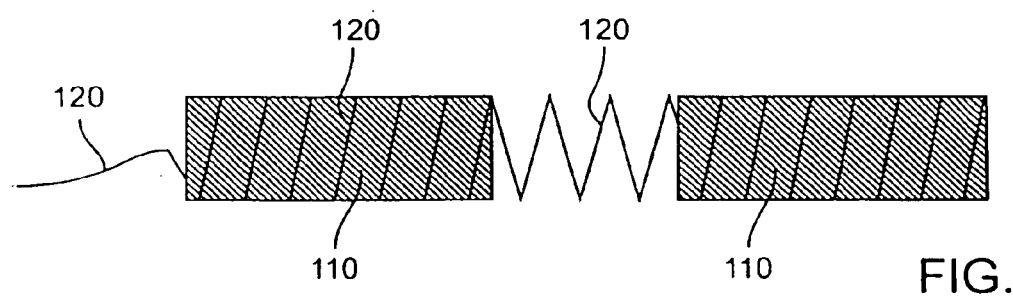
FIG. 15 is an illustration of a two tubular transducers, with a coiled spring positioned in contact with their outer surfaces.

Referring next to FIG. 15, a first spring connector 120 is wrapped around the outer surfaces of successive vibrational transducers 110. In accordance with the present invention, first spring connector 120 exerts an inward pre-loading on each of transducers 110. In preferred aspects, the strength of this inward pre-loading is about 25% to 75% of the breaking (ie: tensile) strength of the transducers. In alternate preferred aspects, the strength of this inward pre-loading is: (a) at least equal to the tensile strength of the transducers; (b) greater than the tensile strength of the transducers, and less than ½ way between the compressive and tensile strengths of the transducers; or (c) approximately ½ way between the compressive and tensile strengths of the transducers. In this aspect of the invention, first spring connector 120 is a form of "restraint" (as described herein), functioning similar to wire 14 or jacket 12.

Figure 14:
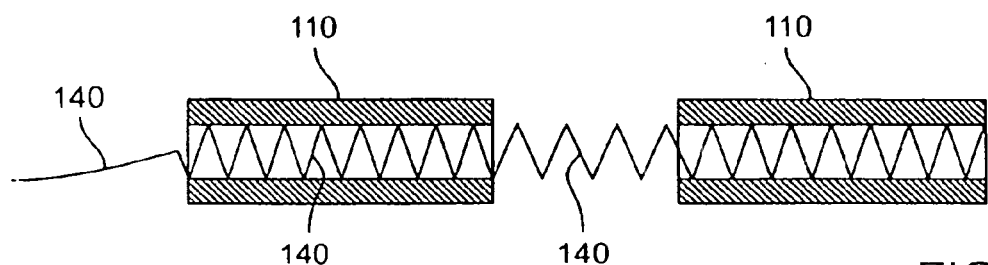
FIG. 14 is an illustration of a two tubular shaped transducers (shown in sectional view), with a coiled spring positioned in contact with their inner surfaces.

Referring next to FIG. 14, a second connector 140 is disposed in contact with the inner surfaces of successive vibrational transducers 110. Preferably, second connector 140 comprises a spring (as illustrated), but it need not comprise a spring. For example, it may comprise a simple electrical lead similar to lead 24 in FIG. 7A.

In various aspects, each of first spring connector 120 and second connector 140 may be connected to respective outer and inner surfaces of transducers 110 by techniques including gluing, soldering, welding or bonding. Additionally, the natural tendency of a spring to "re-coil" or "spring back" into position after it has been deformed may be used to connect the first spring connector 120 and second connector 140 to the transducer surfaces, as follows.

First, the outer spring connector 120 can be unwound such that it expands in diameter, and then be slipped over the transducers, and allowed to contract, tightening around the transducers. Specifically, the wrapping of first spring connector 120 around the outer surfaces of transducers 110 may be accomplished by unwinding first spring connector 102 such that expands in diameter; slipping first spring connector 120 over the outer surfaces of transducers 110 when first spring connector 120 is in an expanded state; and then allowing first spring connector 120 to contract around the outer surfaces of transducers 110, such that first spring connector exerts an inward pre-stress on the outer surfaces of the vibrational transducers.

Secondly, second connector 140 can be tightly wound such that it shrinks in diameter, and then be slipped through the bores through the respective transducers, and then be allowed to expand, tightening against the inner surface of the bore through the respective transducers. Specifically, the positioning of second spring connector 140 in contact with the inner surfaces of vibrational transducers 110 may be accomplished by winding second spring connector 140 such that contracts in diameter; slipping second spring connector 140 through the inner surfaces of successive transducers 110 when second spring connector 140 is in a contracted state; and then allowing second spring connector 140 to expand such that it contacts the inner surfaces of transducers 110.

In various preferred aspects, each of the first spring connector 120 and second connector 140 may comprise singular or multifiliar wraps. Such multifiliar wraps offer the advantages of increased electrical current carrying capacity with increasing overall stiffness.

In various preferred aspects, each of the first spring connector 120 and second connector 140 may be spring having a varying pitch (along its length). Such a varying pitch spring is illustrated in FIG. 16 which shows a tight or narrow pitch for second connector 140 in region 140a (i.e.: within transducer 110) and a lose or wide pitch for second connector 140 in region 140b (i.e.: between two transducers 110). (It is to be understood that spring connector 120 may also have a similar varying pitch in which its coils are spaced closer together when passing over the surface of transducer 110 and are spaced farther apart in regions between successive transducers).

Advantages of varying the spring coil pitch (for either of spring connector 120 or second connector 140) include, but are not limited to, the following. First, a greater percentage of the spring coil can be positioned in direct contact with the outer or inner surface of the transducer. This increases the effectiveness of the electrical contact made by the spring coil to the transducer. Secondly, the greater pitch between transducers results in less electrical resistance and therefore less energy loss due to heating.

Figure 16A:
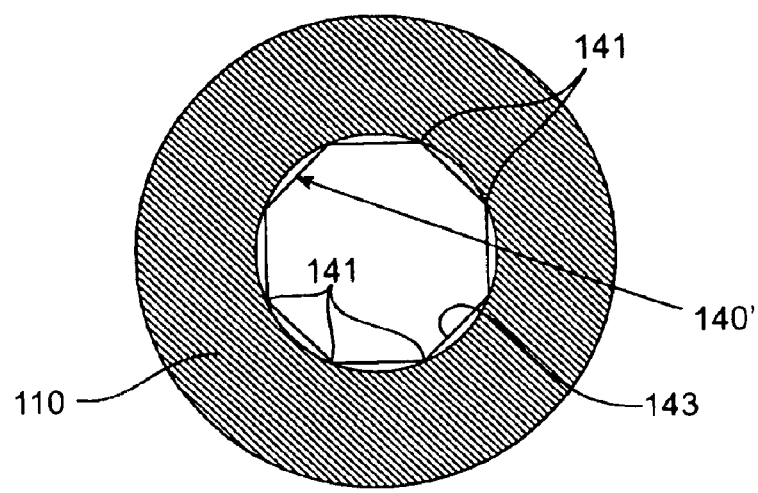
FIG. 16A is a cross-sectional view of a vibrational transducer according to the present invention having a spring coil inner connector with multiple deflection points to provide enhanced electrical contact.

The inner coil 140 may be modified to have multiple deflection points to provide enhanced electrical contact with an inner surface of the vibrational transducer, as shown in FIG. 16A. There, the inner coil 140ρ is bent, kinked, or otherwise deformed to have a plurality of deflection points 141 along its length. Typically, the deflection points will be equally spaced apart, but such equal spacing is not necessary. The deflection points will be oriented so that when the connector 140 is coiled to form a desired spring coil, the deflection points will be oriented radially outward. In this way, as the spring coil is released within the inner passage of the transducer 110, the coil will expand so that the deflection points 141 firmly contact the inner surface 143 of the transducer.

Figure 16B:
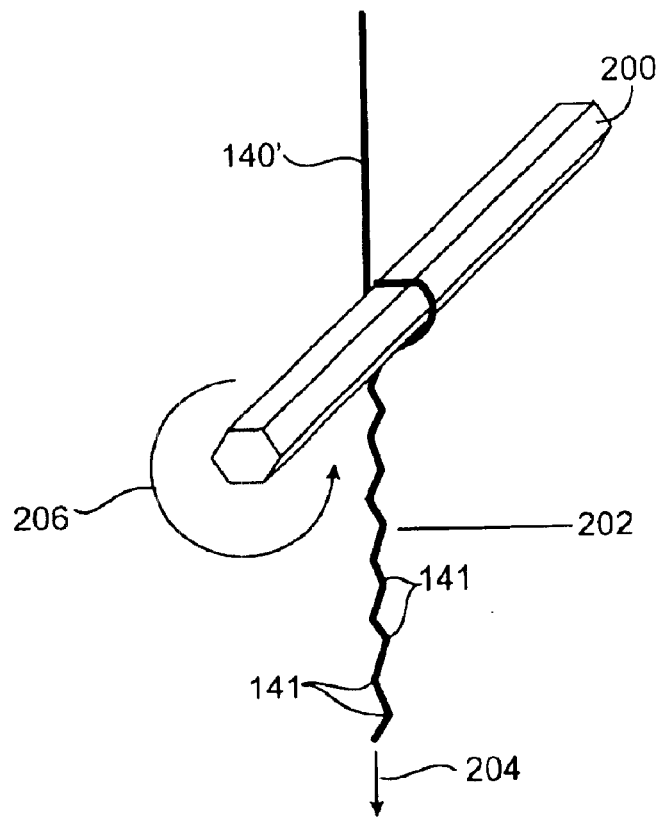
FIG. 16B illustrates an exemplary method for forming a wire with multiple deflection points which may be then formed into the spring coil connector of FIG. 16A.

Referring now to FIG. 16B, an exemplary technique for forming an inner conductor having multiple deflection points is illustrated. A suitable wire, for example, a beryllium cooper wire ribbon (0.001 inch by 0.003 inch) is pulled over a shaped mandrel 200. As illustrated, the mandrel has a hexagonal cross-section, and that other polygonal and irregular shaped mandrels could be used. The wire 202 is pulled in the direction of arrow 204 with a tensile force in the range from 20 grams to 100 grams. As the wire 202 is pulled, the mandrel 200 is turned in the direction of arrow 206 at a rate which matches the axial advancement of the wire 202. In this way, the deflection points 141 are formed in the wire which may then be coiled and placed into the transducer 110, as shown in FIG. 16A.

The present catheter 100 can be used for delivering vibrational energy to a patient. This can be accomplished as follows. Catheter 100 can be introduced into a patient, with first spring connector 120 disposed in contact with outer surfaces of vibrational transducers 110, (exerting an inward pre-loading on the vibrational transducers 110), and with second connector 140 disposed in contact with inner surfaces of transducers 110. Thereafter, transducers 110 can be energized to deliver vibrational energy to the patient. In optional preferred aspects, transducers 110 are operated at a Mechanical Index (MI) of at least 1.9; and at a frequency of at least 500 KHz, but not exceeding 3 MHz. In optional preferred aspects, the inner bores of transducers 110 may be cooled with a cooling flow, which may optionally comprise saline.

What is claimed is:

1. A therapeutic ultrasound delivery system, comprising:
   a catheter body;
   a plurality of axially spaced-apart hollow cylindrical vibrational transducers disposed along a length of the catheter body said transducers having outer and inner surfaces;
   an outer restraint disposed around the outer surfaces of the vibrational transducers, the outer restraint exerting an inward pre-stress on the outer surfaces of the vibrational transducers; and
   an inner spring coil connector disposed in contact with the inner surfaces of the vibrational transducers.

2. The system of claim 1, wherein the inner spring coil has multiple deflection points which provide enhanced electrical contact with the inner surfaces of the vibrational transducers.

3. The system of claim 2, wherein the outer restraint is attached to the outer surface of the vibrational transducers by one of the group consisting of gluing, soldering, welding or bonding.

4. The system of claim 2, wherein the inner connector is attached to the inner surface of the vibrational transducers by one of the group consisting of gluing, soldering, welding or bonding.

5. The system of claim 2, wherein the inner and outer surfaces of the vibrational transducers are metallic.

6. The system of claim 2, wherein at least one of the outer restraint and inner connector comprises a single filament wrap.

7. The system of claim 2, wherein at least one of the outer restraint and inner connector comprises a multifiliment wrap.

8. The system of claim 2, wherein the outer restraint exerts an inward pre-stress equal to about 25% to 75% of the breaking strength of the transducers.

9. The system of claim 2, wherein the outer restraint exerts an inward pre-stress at least equal to the tensile strength of the transducers.

10. The system of claim 2, wherein the outer restraint exerts an inward pre-stress that is greater than the tensile strength of the transducers, and less than the average of the compressive and tensile strengths of the transducers.

11. The system of claim 2, wherein the outer restraint exerts an inward pre-stress that is approximately equal to the average of the compressive and tensile strengths of the transducers.

12. The system of claim 2, wherein the vibrational transducers are made from the group consisting of a piezoelectric ceramic, an electrostrictive ceramic and a piezoelectric crystal.

13. The system of claim 12, wherein the vibrational transducers are made from the group consisting of PZT-8 and PZT-4 ceramic material.

14. The system of claim 2, wherein the outer restraint is a spring.

15. The system of claim 2, wherein the inner spring coil connector pushes gently outwardly against the inner surfaces of the vibrational transducers.

16. The system of claim 14, wherein the pitch of the spring is less in regions adjacent each of the individual transducers than in regions between each of the individual transducers.

17. The system of claim 2, wherein the pitch of the inner spring coil is less in regions within the inner bores of each of the individual transducers than in regions between each of the individual transducers.

18. The system of claim 2, wherein the outer restraint is made from a material having a Young's Modulus in the range of 10,000,000 psi to 70,000,000.

19. The system of claim 2, wherein the outer restraint is made from a material having a tensile strength in the range of 50,000 psi to 400,000.

20. The system of claim 2, wherein the outer restraint is made from a material having electrical conduction properties in the range of 9 to 100 ohms per mil:ft.

21. The system of claim 2, wherein at least one of the outer restraint or inner connector is made from a material selected from the group consisting of beryllium copper alloys, steel alloys, aluminum alloys, nickel alloys, nickel titanium alloys and tungsten alloys.

22. The system of claim 2, wherein the outer restraint is disposed around the outer surfaces of two successive vibrational transducers.

23. The system of claim 2, wherein the outer restraint is disposed around the outer surfaces of three successive vibrational transducers.

24. The system of claim 2, wherein the outer restraint is disposed around the outer surfaces of all of the transducers in the catheter body.

25. A method of assembling a system for delivering vibrational energy to a patient, comprising:

providing a catheter body;

providing a plurality of axially spaced apart hollow cylindrical vibrational transducers disposed along a length of the catheter body;

connecting together the plurality of hollow cylindrical vibrational transducers within the catheter body by:
wrapping a first spring connector around the outer surfaces of the vibrational transducers wherein the first spring connector exerts an inward pre-stress on the outer surfaces of the vibrational transducers; and
positioning a second spring coil connector in contact with the inner surfaces of the vibrational transducers, wherein the second spring coil connector has multiple deflection points which contact the inner surfaces.

* * * * *